(12) United States Patent
Goredema et al.

(10) Patent No.: US 7,973,186 B1
(45) Date of Patent: Jul. 5, 2011

(54) LOW MOLECULAR WEIGHT PIGMENT DISPERSANTS FOR PHASE CHANGE INK

(75) Inventors: Adela Goredema, Mississauga (CA); Mihaela Maria Birau, Mississauga (CA); C. Geoffrey Allen, Waterdown (CA); Caroline Turek, Mississauga (CA); Maxine E. Haberl, Burnaby (CA); Carol A. Jennings, Toronto (CA); Peter G. Odell, Mississauga (CA)

(73) Assignee: Xerox Corporation, Norwalk, CT (US)

( * ) Notice: Subject to any disclaimer, the term of this patent is extended or adjusted under 35 U.S.C. 154(b) by 0 days.

(21) Appl. No.: 12/641,564

(22) Filed: Dec. 18, 2009

(51) Int. Cl.
*C07C 233/05* (2006.01)
*C07C 231/02* (2006.01)

(52) U.S. Cl. .............................. 554/51; 554/37; 564/143

(58) Field of Classification Search .................... 554/51, 554/37; 564/143
See application file for complete search history.

(56) References Cited

U.S. PATENT DOCUMENTS

| | | | |
|---|---|---|---|
| 3,996,059 A | 12/1976 | Stansfield et al. | |
| 6,174,937 B1 | 1/2001 | Banning et al. | |
| 6,309,453 B1 | 10/2001 | Banning et al. | |
| 6,547,380 B2 | 4/2003 | Smith et al. | |
| 6,858,070 B1 | 2/2005 | Wong et al. | |
| 6,860,930 B2 | 3/2005 | Wu et al. | |
| 6,878,198 B1 | 4/2005 | Drappel et al. | |
| 7,635,731 B2 * | 12/2009 | Sigworth et al. | 524/13 |
| 2004/0132862 A1 | 7/2004 | Woudenberg | |
| 2007/0119340 A1 | 5/2007 | Breton et al. | |
| 2007/0120924 A1 | 5/2007 | Odell et al. | |
| 2007/0123606 A1 | 5/2007 | Toma et al. | |
| 2007/0203272 A1 | 8/2007 | Heinrichs | |
| 2008/0098927 A1 | 5/2008 | Allen et al. | |
| 2009/0038506 A1 | 2/2009 | Odell et al. | |
| 2009/0082489 A1 | 3/2009 | Breton et al. | |
| 2010/0028537 A1 | 2/2010 | Goredema et al. | |

FOREIGN PATENT DOCUMENTS

JP 10-88489 * 4/1998
WO WO 01/23481 A1 4/2001

OTHER PUBLICATIONS

Commonly Assigned, co-pending U.S. Patent Application filed Dec. 18, 2009, of Adela Goredema et al., entitled "Pigmented Phase Change Inks Containing Low Molecular Weight Pigment Dispersants" 66 pages, U.S. Appl. No. 12/641,609.
Commonly Assigned, co-pending U.S. Patent Application filed Feb. 11, 2010, of Marcel P. Breton et al., entitled "Process for Preparing Stable Pigmented Curable Solid Inks" 42 pages, U.S. Appl. No. 12/703,817.
Commonly Assigned, co-pending U.S. Patent Application filed May 18, 2009, of Adela Goredema et al., entitled "Low Molecular Weight Quaternary Ammonium Salt Dispersants" 46 pages, U.S. Appl. No. 12/467,692.
Commonly Assigned, co-pending U.S. Patent Application filed May 18, 2009, of Adela Goredema et al., entitled "Pigmented Phase Change Inks Containing Low Molecular Weight Quaternary Ammonium Salt Dispersants," 45 pages, U.S. Appl. No. 12/467,769.
Commonly Assigned, co-pending U.S. Patent Application filed Sep. 23, 2009, of Adela Goredema et al., entitled "Ink Carriers Containing Low Viscosity Functionalized Waxes, Phase Change Inks Including Same, and Methods For Making Same," 48 pages, U.S. Appl. No. 12/236,029.

* cited by examiner

*Primary Examiner* — Shailendra Kumar
(74) *Attorney, Agent, or Firm* — Marylou J. Lavoie, Esq. LLC

(57) ABSTRACT

Disclosed is a compound of the formula

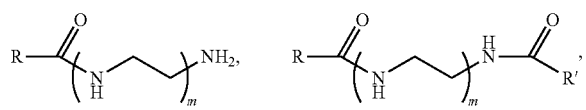

or a mixture thereof; wherein R and R' are the same or different, and wherein R and R' are independently selected from an alkyl group, an arylalkyl group, or an alkylaryl group, wherein the alkyl group, the arylalkyl group, or the alkylaryl group has from about 18 to about 60 carbon atoms; and wherein m is an integer of from about 1 to about 30.

17 Claims, 4 Drawing Sheets

LOW MOLECULAR WEIGHT PIGMENT DISPERSANTS FOR PHASE CHANGE INK

TECHNICAL FIELD

Described herein are dispersants for inks such as solid phase change or hot melt inks that may be used in a number of copying and printing devices. More particularly, described herein are dispersant compounds comprising first functional groups that anchor the dispersant to the pigment particles and second functional groups that are compatible with the ink vehicle, methods of making such compounds, and inks containing these compounds.

RELATED APPLICATIONS

Commonly assigned U.S. patent application Ser. No. 12/641,609 (entitled "Pigmented Phase Change Inks Containing Low Molecular Weight Pigment Dispersants"), filed concurrently herewith, which is hereby incorporated by reference herein in its entirety, describes phase change inks including a dispersant compound used to stabilize pigment particles.

BACKGROUND

Ink jetting devices are well known in the art. Ink jet printing systems are generally of two types: continuous stream and drop-on-demand. In continuous stream ink jet systems, ink is emitted in a continuous stream under pressure through at least one orifice or nozzle. The stream is perturbed, causing it to break up into droplets at a fixed distance from the orifice. At the break-up point, the droplets are charged in accordance with digital data signals and passed through an electrostatic field that adjusts the trajectory of each droplet in order to direct it to a gutter for recirculation or a specific location on a recording medium. In drop-on-demand systems, a droplet is expelled from an orifice directly to a position on a recording medium in accordance with digital data signals. A droplet is not formed or expelled unless it is to be placed on the recording medium. There are generally three types of drop-on-demand ink jet systems. One type of drop-on-demand system is a piezoelectric device that has as its major components an ink filled channel or passageway having a nozzle on one end and a piezoelectric transducer near the other end to produce pressure pulses. Another type of drop-on-demand system is known as acoustic ink printing. As is known, an acoustic beam exerts a radiation pressure against objects upon which it impinges. Thus, when an acoustic beam impinges on a free surface (i.e., liquid/air interface) of a pool of liquid from beneath, the radiation pressure which it exerts against the surface of the pool may reach a sufficiently high level to release individual droplets of liquid from the pool, despite the restraining force of surface tension. Focusing the beam on or near the surface of the pool intensifies the radiation pressure it exerts for a given amount of input power. Still another type of drop-on-demand system is known as thermal ink jet, or bubble jet, and produces high velocity droplets. The major components of this type of drop-on-demand system are an ink filled channel having a nozzle on one end and a heat generating resistor near the nozzle. Printing signals representing digital information originate an electric current pulse in a resistive layer within each ink passageway near the orifice or nozzle, causing the ink vehicle (usually water) in the immediate vicinity to vaporize almost instantaneously and create a bubble. The ink at the orifice is forced out as a propelled droplet as the bubble expands.

In a typical design of a piezoelectric ink jet device, the image is applied by jetting appropriately colored inks during four to eighteen rotations (incremental movements) of a substrate such as an image receiving member or intermediate transfer member with respect to the ink jetting head, i.e., there is a small translation of the printhead with respect to the substrate in between each rotation. This approach simplifies the printhead design, and the small movements ensure good droplet registration. At the jet operating temperature, droplets of liquid ink are ejected from the printing device and, when the ink droplets contact the surface of the recording substrate, either directly or via an intermediate heated transfer belt or drum, they quickly solidify to form a predetermined pattern of solidified ink drops.

Ink jet printing processes may employ inks that are solid at room temperature and liquid at elevated temperatures. Such inks may be referred to as hot melt inks or phase change inks. In thermal ink jet printing processes employing hot melt inks, the solid ink is melted by the heater in the printing apparatus and utilized (i.e., jetted) as a liquid in a manner similar to that of conventional thermal ink jet printing. Upon contact with the printing substrate, the molten ink solidifies rapidly, enabling the colorant to substantially remain on the surface of the substrate instead of being carried into the substrate (for example, paper) by capillary action, thereby enabling higher print density than is generally obtained with liquid inks. Advantages of a phase change ink in ink jet printing are thus elimination of potential spillage of the ink during handling, a wide range of print density and quality, minimal paper cockle or distortion, and enablement of indefinite periods of non-printing without the danger of nozzle clogging, even without capping the nozzles.

Current phase change inks often comprise custom dye colorants. These custom dyes are very expensive. It is desired to replace custom dye colorants with less expensive colorants. Pigments are typically much less expensive than dye colorants. In addition, pigments can offer improved colorfastness over dyes, reduce or eliminate migration issues, and improve ink robustness characteristics.

Pigmented phase change ink compositions that include various dispersants are also known. However, the use of polymeric dispersants is not favored in some phase change inks for a variety of reasons. The problems caused by the use of polymeric dispersants include a negative effect on rheological properties of the ink, such as non-Newtonian behavior and an increase in viscosity.

Pigment particles in the ink must be properly dispersed and stabilized such that the ink can be reliably jetted without the clogging of the printheads by the pigment particles. Polymeric dispersants in phase change inks also affect drop formation, because polymers will tend to form filaments which affect the formation of small drop sizes. Most of the commercially available dispersants were designed for aqueous based and solvent based ink systems and are not compatible with hydrophobic wax based inks. Many of the commercially available compounds that can effect dispersion of pigments in low polarity inks (usually solvent-based) are liquids or pastes and are not designed to chemically withstand the excessive temperatures in the printer (115 to 120° C.) for long periods of time. Furthermore, the use of polymers in solid ink is not favored for the following reasons: a) they have a negative impact on rheological properties producing non-Newtonian behavior and an increase in viscosity, b) they affect drop formation during jetting, polymers will tend to form filaments which might affect the formation of small drop sizes.

While known compositions and processes are suitable for their intended purposes, a need remains for pigment stabilizing resinous compounds that are chemically stable, are compatible with the phase change ink formulation and that can provide stabilization of pigment particles in phase change inks over long periods of time at high temperatures. There is further a need for an improved colored phase change ink composition. For example, there remains a need for phase change inks with pigment colorants where the pigment particles are stable and well dispersed in the ink. There remains a need for pigmented phase change inks with improved image quality, improved light fastness, and reduced show through. A need also remains for pigmented phase change inks where the colorants have reduced agglomeration and settling in the ink when the ink is exposed to high temperatures for prolonged periods. A need also remains for pigmented phase change inks with reduced clogging of the jets in the printhead.

SUMMARY

Described is a dispersant compound of the formula

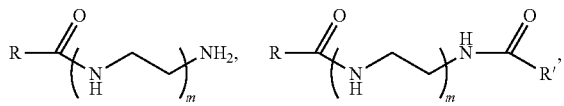

or a mixture thereof; wherein R and R' are the same or different, and wherein R and R' are independently selected from: (i) an alkyl group, which may be linear or branched, cyclic or acyclic, substituted or unsubstituted, and wherein hetero atoms either may or may not be present in the alkyl group; (ii) an arylalkyl group, which may be substituted or unsubstituted, wherein the alkyl portion of the arylalkyl group can be linear or branched, cyclic or acyclic, substituted or unsubstituted, and wherein hetero atoms either may or may not be present in either the aryl or the alkyl portion of the arylalkyl group; or (iii) an alkylaryl group, which may be substituted or unsubstituted, wherein the alkyl portion of the alkylaryl group can be linear or branched, cyclic or acyclic, substituted or unsubstituted, and wherein hetero atoms either may or may not be present in either the aryl or the alkyl portion of the alkylaryl group; wherein the alkyl group, the arylalkyl group, or the alkylaryl group has from about 18 to about 60 carbon atoms; and wherein m is an integer of from about 1 to about 30.

Also described is a method for preparing a dispersant compound comprising melting a carboxylic acid of the formula

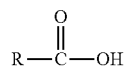

wherein R is (i) an alkyl group, which may be linear or branched, cyclic or acyclic, substituted or unsubstituted, and wherein hetero atoms either may or may not be present in the alkyl group, (ii) an arylalkyl group, which may be substituted or unsubstituted, wherein the alkyl portion of the arylalkyl group can be linear or branched, cyclic or acyclic, substituted or unsubstituted, and wherein hetero atoms either may or may not be present in either the aryl or the alkyl portion of the arylalkyl group, or (iii) an alkylaryl group, which may be substituted or unsubstituted, wherein the alkyl portion of the alkylaryl group can be linear or branched, cyclic or acyclic, substituted or unsubstituted, and wherein hetero atoms either may or may not be present in either the aryl or the alkyl portion of the alkylaryl group; under an inert atmosphere; wherein the alkyl group, the arylalkyl group, or the alkylaryl group has from about 18 to about 60 carbon atoms; and reacting an amine compound of the formula

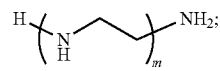

wherein m is an integer of from about 1 to about 30, with the melted carboxylic acid, under an inert atmosphere and at an elevated temperature of about 170 to about 200° C.;

wherein the carboxylic acid and the amine are provided in a 2:1 ratio of carboxylic acid to amine, to provide a product of the formula

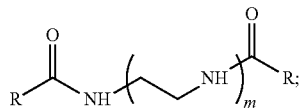

when the carboxylic acid and the amine are provided in a 1:1 ratio of carboxylic acid to amine; or to provide a product of the formula

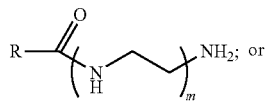

in further embodiments, wherein the carboxylic acid and the amine are provided in a carboxylic acid to amine ratio that is less than 2 but greater than 1, for example, a 1.5:1 ratio of carboxylic acid to amine, to provide a product comprising a mixture of the formula

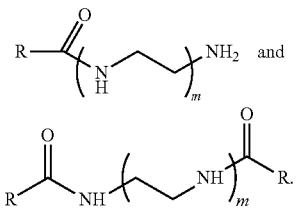

DETAILED DESCRIPTION

Figure 1:
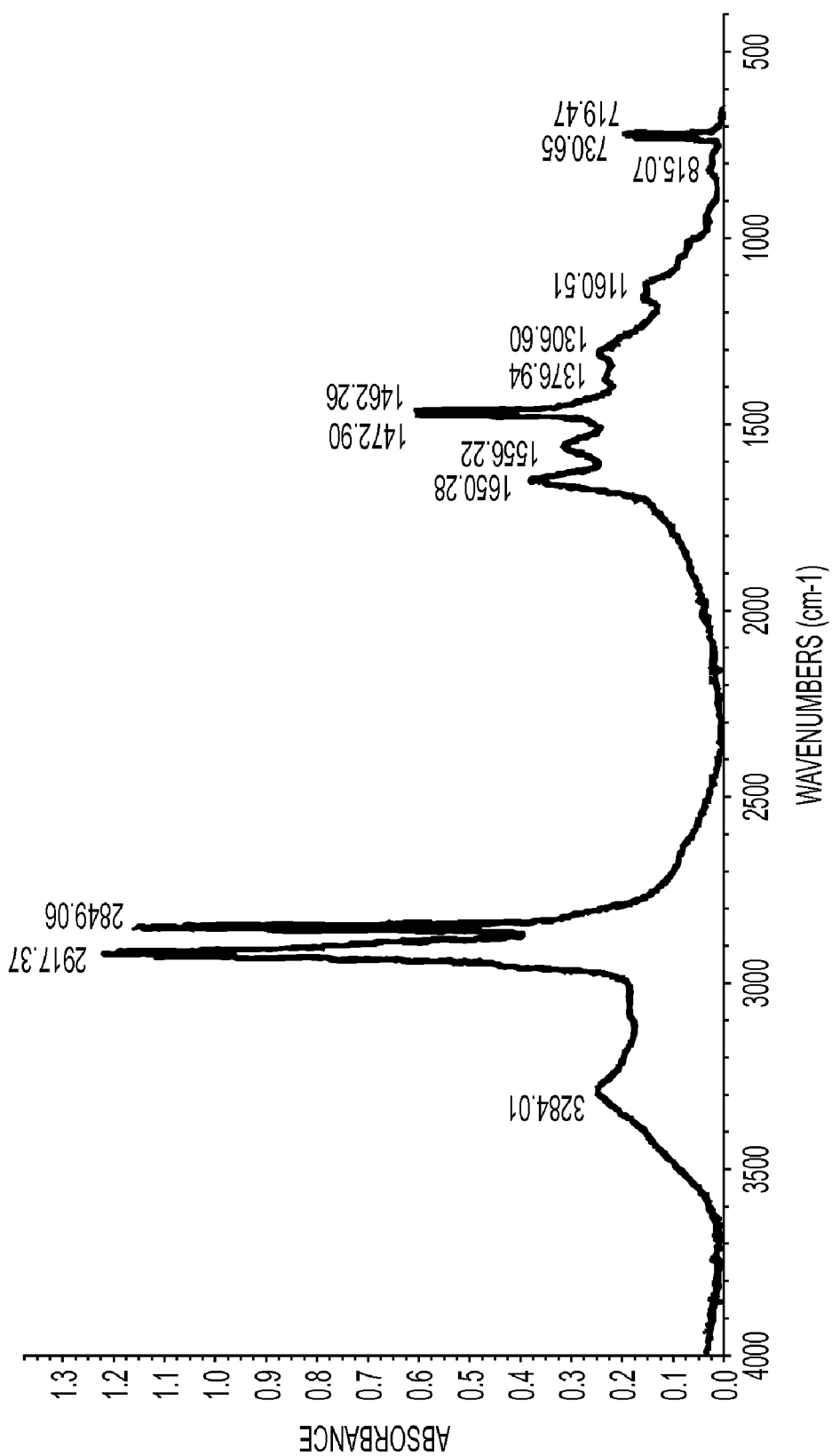
FIG. 1 is a graph illustrating an infrared spectra of a dispersant of the present disclosure.
Figure 2:
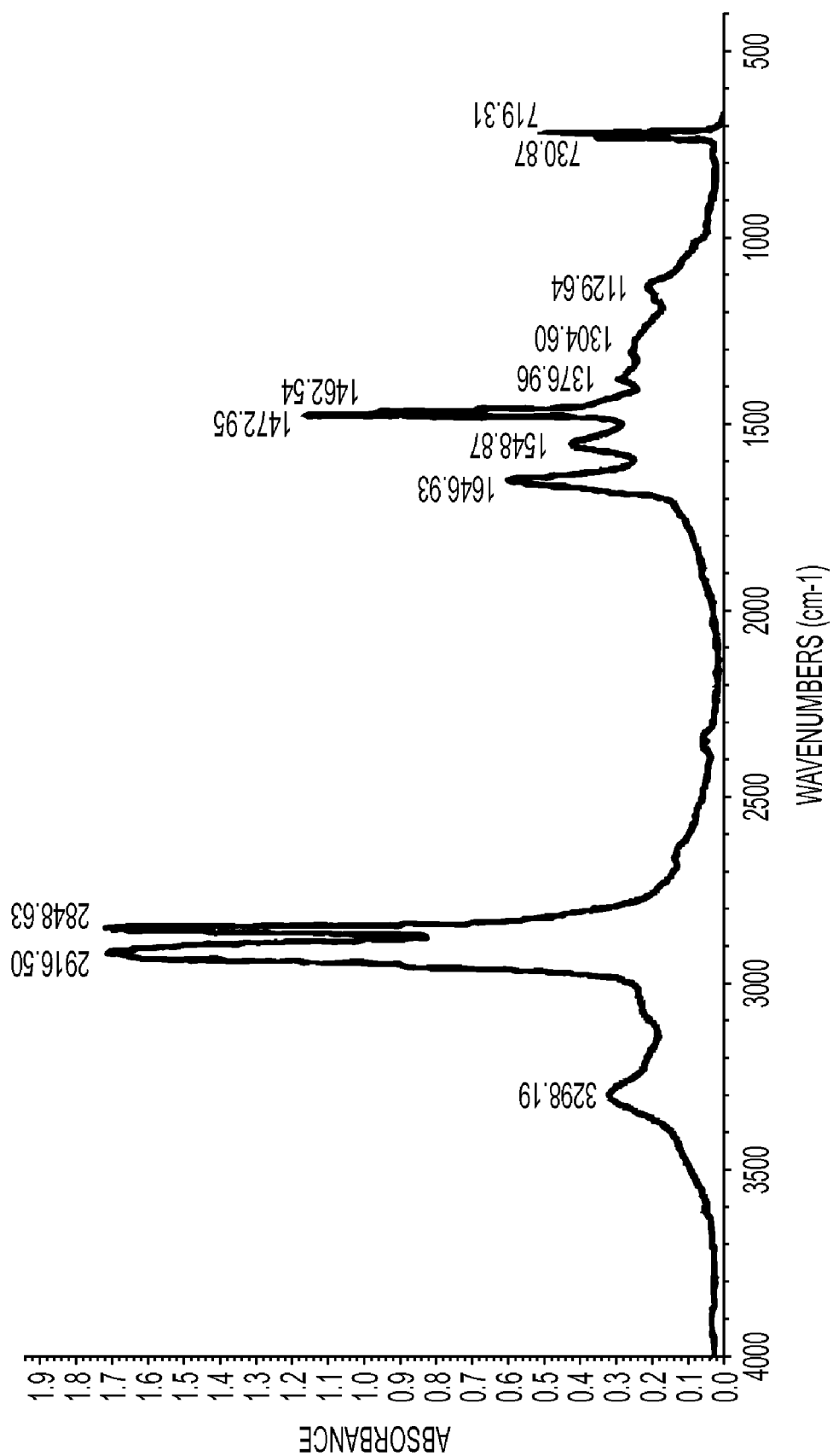
FIG. 2 is a graph illustrating an infrared spectra of another dispersant of the present disclosure.
Figure 3:
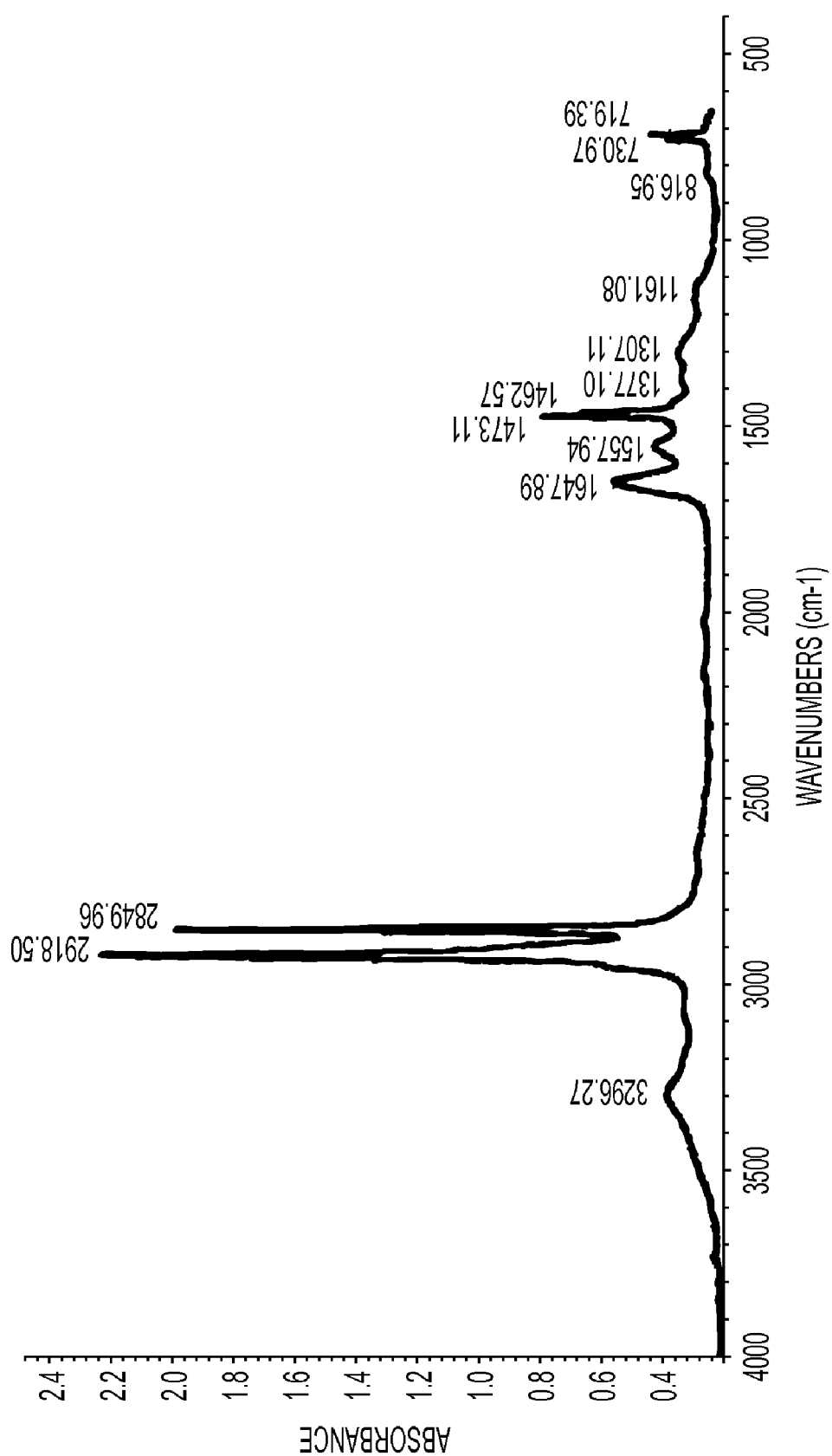
FIG. 3 is a graph illustrating an infrared spectra of yet another dispersant of the present disclosure.
Figure 4:
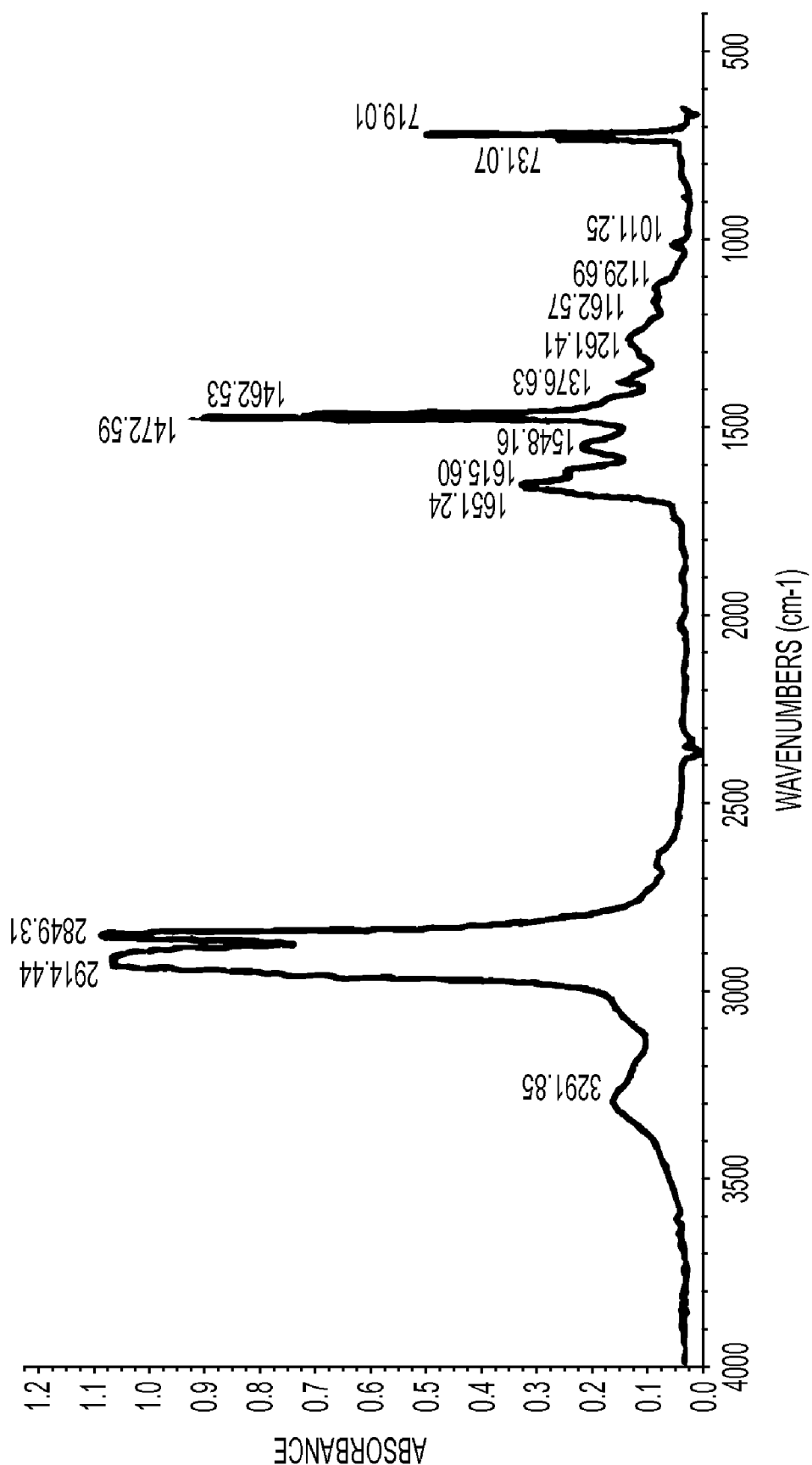
FIG. 4 is a graph illustrating an infrared spectra of still another dispersant of the present disclosure.

This disclosure is not limited to particular embodiments described herein, and some components and processes may be varied by one of ordinary skill in the art, based on this disclosure. The terminology used herein is for the purpose of described particular embodiments only, and is not intended to be limiting.

In embodiments, compounds are provided herein which can be used as pigment dispersants for phase change inks. Pigments are known to be hard to disperse in most media due to pigment aggregation and agglomeration. Solid or phase change ink contains non-polar waxes and is used in a high temperature environment with printheads operating at approximately 120° C. which has a destabilizing influence on the pigment dispersion. Compounds herein provide two characteristics: 1) a hydrophobic chain that provides steric stabilization in the required medium, this feature can be termed the "brush", and 2) capability to be strongly adsorbed (or anchored) to the pigment surface through an anchor group. While not wishing to be bound by theory, the present authors believe the present disclosure provides a system wherein a pigment particle is disposed in a medium and is stabilized with a stabilizer or dispersant comprising an anchor group which is anchored, such as adsorbed, attached, or grafted, to the pigment particle and a stabilizing group (or brush group) which is compatible with the ink vehicle. The anchor group can anchor by any suitable way to the pigment particle such as by van der Waals' forces or hydrogen bonding of the amine to hydrogen. The brush group can comprise a waxy, hydrophobic chain that is compatible with the ink vehicle. The brush groups further prevent pigment particle agglomeration by repelling other pigment-dispersant pairs so as to hinder particle agglomeration thereby enabling the average pigment particle size to remain at a desired small value.

Further, while not wishing to be bound by theory, the present authors believe the present pigment particle dispersant system provides that a pigment particle is dispersed in a medium and a dispersant is anchored to the pigment particle via an anchor group while brush groups serve as steric stabilization chains. If two particles approach each other, the layers of the adsorbed material start to overlap, and when steric stabilization occurs, the layers effectively repel each other; thereby keeping the pigments well dispersed in the medium.

In embodiments, a dispersant can include single anchor group and a single brush group, or, a single anchor group and first and second brush groups.

In embodiments, pigment dispersants for phase change inks are provided comprising brush components comprising long, waxy chains, such as polyethylene based, which are compatible with non-polar wax based inks and an anchoring unit comprising amine groups that strongly adsorb (anchor) to the pigment particles and to keep the particles dispersed even at high temperatures (>100° C.) such as are used in solid or phase change ink printers. In embodiments, the present dispersants include a brush comprising a waxy carboxylic acid having a chain length of from about 18 to about 60 carbon atoms, or from about 21 to about 47 carbon atoms, or from about 30 to about 47 carbon atoms, although the number of carbon atoms can be outside of these ranges. In further embodiments, the dispersants include an amine anchoring unit.

In embodiments, dispersants herein successfully dispersed pigment, such as magenta pigment Red 57:1, providing inks that show no particle size growth for over one year. In further embodiments, inks containing the present dispersants are stable after being aged in an ink jet printer for over 10 days.

In embodiments, a compound of the formula

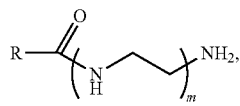

-continued

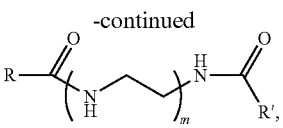

or a mixture thereof, is provided, wherein R and R' are each independently selected from: (i) an alkyl group, which may be linear or branched, cyclic or acyclic, substituted or unsubstituted, and wherein hetero atoms such as oxygen, nitrogen, sulfur, silicon, phosphorus and the like either may or may not be present in the alkyl group, in one embodiment with at least about 1 carbon atom, in another embodiment with at least about 16 carbon atoms, and in yet another embodiment with at least about 23 carbon atoms, and in one embodiment with no more than about 200 carbon atoms, in another embodiment with no more than about 150 carbon atoms, and in yet another embodiment with no more than about 100 carbon atoms, although the number of carbon atoms can be outside of these ranges, (ii) an arylalkyl group, which may be substituted or unsubstituted, wherein the alkyl portion of the arylalkyl group can be linear or branched, cyclic or acyclic, substituted or unsubstituted, and wherein hetero atoms such as oxygen, nitrogen, sulfur, silicon, phosphorus and the like either may or may not be present in either the aryl or the alkyl portion of the arylalkyl group, in one embodiment with at least about 6 carbon atoms, and in another embodiment with at least about 23 carbon atoms, and in one embodiment with no more than about 200 carbon atoms, in another embodiment with no more than about 150 carbon atoms, and in yet another embodiment with no more than about 100 carbon atoms, although the number of carbon atoms can be outside of these ranges; or (iii) an alkylaryl group, which may be substituted or unsubstituted, wherein the alkyl portion of the alkylaryl group can be linear or branched, cyclic or acyclic, substituted or unsubstituted, and wherein hetero atoms such as oxygen, nitrogen, sulfur, silicon, phosphorus and the like either may or may not be present in either the aryl or the alkyl portion of the alkylaryl group, in one embodiment with at least about 6 carbon atoms, and in another embodiment with at least about 23 carbon atoms, and in one embodiment with no more than about 200 carbon atoms, in another embodiment with no more than about 150 carbon atoms, and in yet another embodiment with no more than about 100 carbon atoms, although the number of carbon atoms can be outside of these ranges, and wherein m is an integer of from about 1 to about 30.

In embodiments, R and R' are the same or different and R and R' are each independently selected from a linear alkyl group having from about 18 to about 60 carbon atoms, or from about 21 to about 47 carbon atoms, or from about 30 to about 47 carbon atoms. In one specific embodiment, R and R' are independently selected from a linear alkyl group having about 21 carbon atoms. In another specific embodiment, R and R' are independently selected from a linear alkyl group having about 30 carbon atoms. In yet another specific embodiment, R and R' are independently selected from a linear alkyl group having about 37 carbon atoms. In another specific embodiment, R and R' are independently selected from a linear alkyl group having about 47 carbon atoms.

The anchoring group herein can be any suitable anchoring group. In embodiments, the anchoring group comprises a compound of the formula

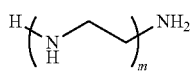

wherein m is an integer of from about 1 to about 30, or from about 1 to about 20. In a specific embodiment, m is from about 1 to about 14.

In embodiments, the compound herein is of the formula

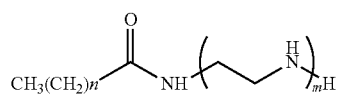

wherein n is an integer of from about 20 to about 46 and m is an integer of from about 1 to about 14; or

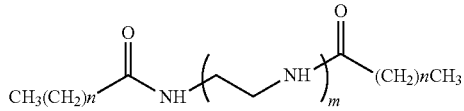

wherein each n is an integer of from about 20 to about 46 and m is an integer of from about 1 to about 14.

In specific embodiments, the compound is of the formula

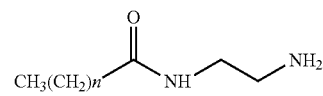

where n has an average value of about 46 carbons;

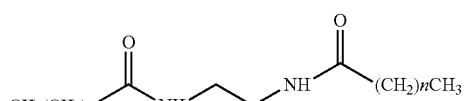

where n has an average value of about 46 carbons;

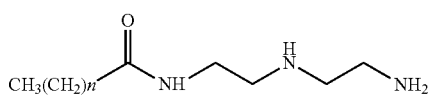

where n has an average value of about 46 carbons;

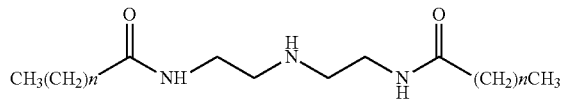

where n has an average value of about 46 carbons;

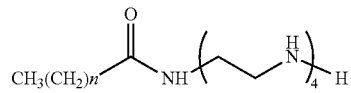

where n has an average value of about 46 carbons;

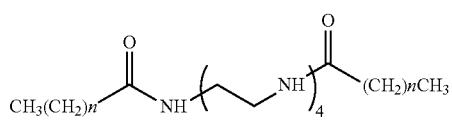

where n has an average value of about 46 carbons;

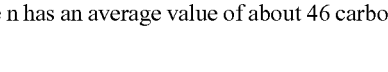

where n has an average value of about 46 carbons and m is about 6;

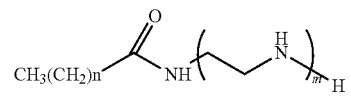

where n has an average value of about 46 carbons and m is about 6;

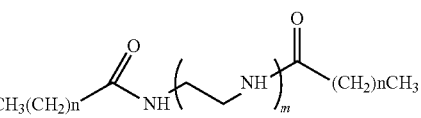

where n has an average value of about 46 carbons and m is about 9;

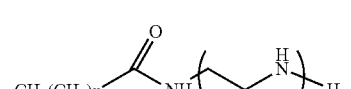

where n has an average value of about 46 carbons and m is about 9;

where n has an average value of about 46 carbons and m is about 14;

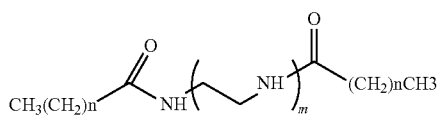

where n has an average value of about 46 carbons and m is about 14;

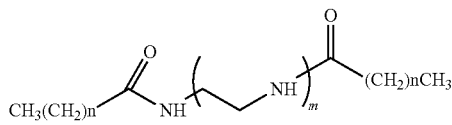

where n has an average value of about 36 carbons and m is about 9;

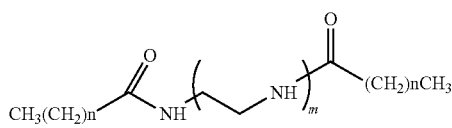

where n has an average value of about 28 carbons and m is about 9; or

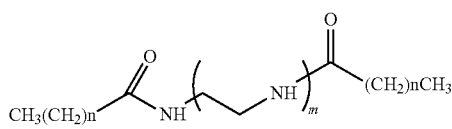

where n has an average value of about 20 carbons and m is about 9; or, in further embodiments, a mixture of the following compounds

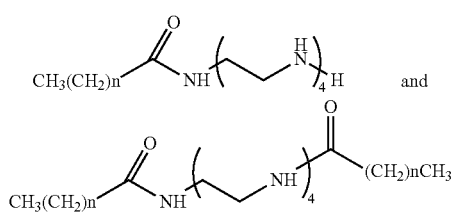

where n has an average value of 46 carbons; or a mixture of

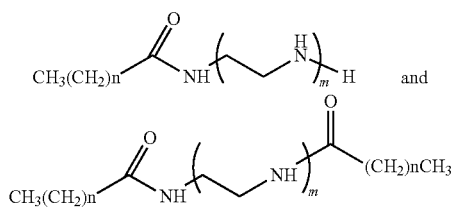

wherein n has an average value of about 46 carbons and wherein m is about 6.

The dispersant compounds herein can be prepared by any suitable method. For example, a method for preparing the compounds herein can comprise melting a carboxylic acid of the formula

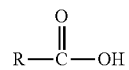

wherein R is (i) an alkyl group, which may be linear or branched, cyclic or acyclic, substituted or unsubstituted, and wherein hetero atoms either may or may not be present in the alkyl group, (ii) an arylalkyl group, which may be substituted or unsubstituted, wherein the alkyl portion of the arylalkyl group can be linear or branched, cyclic or acyclic, substituted or unsubstituted, and wherein hetero atoms either may or may not be present in either the aryl or the alkyl portion of the arylalkyl group, or (iii) an alkylaryl group, which may be substituted or unsubstituted, wherein the alkyl portion of the alkylaryl group can be linear or branched, cyclic or acyclic, substituted or unsubstituted, and wherein hetero atoms either may or may not be present in either the aryl or the alkyl portion of the alkylaryl group; under an inert atmosphere; wherein the alkyl group, the arylalkyl group, or the alkylaryl group has from about 18 to about 60 carbon atoms; and reacting an amine compound of the formula

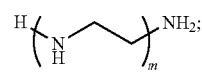

wherein m is an integer of from about 1 to about 30,
with the melted carboxylic acid, under an inert atmosphere and at an elevated temperature of about 170 to about 200° C.;
wherein the carboxylic acid and the amine are provided in a 2:1 ratio of carboxylic acid to amine; or
wherein the carboxylic acid and the amine are provided in a 1:1 ratio of carboxylic acid to amine; or
wherein the carboxylic acid and the amine are provided in a carboxylic acid to amine ratio that is less than 2 but greater than 1, for example, a 1.5:1 ratio of carboxylic acid to amine;
to provide a product of the formula

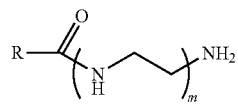

when the carboxylic acid and the amine are provided in a 1:1 ratio of carboxylic acid to amine; or
to provide a product of the formula

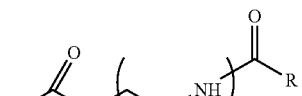

when the carboxylic acid and the amine are provided in a 2:1 ratio of carboxylic acid to amine; or to provide a product comprising a mixture of the formula

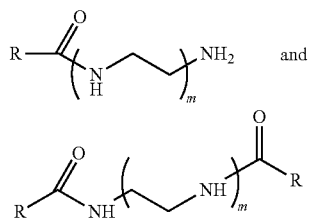

when the carboxylic acid and the amine are provided in a 1.5:1 ratio of carboxylic acid to amine.

The process may include additional process steps. For example, the process can include the removal of water, such as through evaporation or distillation. The process may further include any additional chemical synthesis steps according to the knowledge of a person having ordinary skill in the art.

The carboxylic acid can generally be any carboxylic acid, in embodiments such that the resulting compound has a linear alkyl group R that includes at least 22 carbon atoms. The groups R in the resulting dispersant compound are formed from the carboxylic acid alkyl chain, and therefore the particular carboxylic acid is chosen based on the desired length of R. For example, the carboxylic acid may be a carboxylic acid having an alkyl chain with a number of carbon atoms as is discussed above.

The inert atmosphere can be any atmosphere that does not contain compounds that will react with the compounds in the chemical process. Inert atmospheres are generally known according to the knowledge of a person having ordinary skill in the art. For example, the inert atmosphere may be an atmosphere made up of only a noble gas, such as argon.

The amine can be any suitable amine. In embodiments, the amine is a compound of the formula

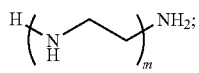

wherein m is an integer of from about 1 to about 30, or from about 1 to about 20, or from about 1 to about 14.

The reaction can be performed neat.

The process can further comprises steps of cooling and isolating the product which steps can be performed according to the knowledge of a person having ordinary skill in the art. Various techniques for these processing steps are known in the chemical arts.

The carboxylic acid and the amine can be provided in any desired or effective amounts. In one embodiment, the carboxylic acid and amine are provided in a 1:1 ratio of carboxylic acid to amine. In another embodiment, the carboxylic acid and the amine are provided in a 1.5:1 ratio of carboxylic acid to amine. In yet another embodiment, the carboxylic acid and amine are provided in a 2:1 ratio of carboxylic acid to amine, although the ratios can be outside of these ranges.

The reaction between the carboxylic acid and the amine compound can be carried out for any desired or effective period of time, in one embodiment at least about 1 hour, in another embodiment at least about 2 hours, and in yet another embodiment at least about 3 hrs, and in another embodiment no more than about 10 hours, although the period of time can be outside of these ranges.

The above discussed dispersant compounds can be used as dispersants in phase change inks. The phrase "used as a dispersant" means that the dispersant compound stabilizes the pigment particles in the ink vehicle by hindering the pigment particles from flocculating into larger agglomerates and thus delay settling. Generally, the dispersant compound achieves this function by adhering to the pigment particles and providing steric stabilization. The dispersant compound adheres to the pigment by, for example, being absorbed, attached or grafted to the pigment particle. In embodiments, the dispersant compound may be present in the ink in an amount of from about 0.1 to about 25 percent by weight of the ink. For example, in a particular embodiment, the dispersant compound may be present in the ink in an amount of from about 1 to about 10 percent by weight, or from about 1 to about 5 percent by weight.

Examples of the phase change inks herein are inks that include an ink vehicle that is solid at temperatures of about 23° C. to about 27° C., for example room temperature, and specifically are solid at temperatures below about 60° C. However, the inks change phase upon heating, and are in a molten state at jetting temperatures. Thus, the inks have a viscosity of from about 1 to about 20 centipoise (cP), for example from about 5 to about 15 cP or from about 8 to about 12 cP, at an elevated temperature suitable for ink jet printing, for example temperatures of from about 60° C. to about 150° C.

In this regard, the inks herein may be either low energy inks or high energy inks. Low energy inks are solid at a temperature below about 40° C. and have a viscosity of from about 1 to about 20 cP such as from about 5 to about 15 cP, for example from about 8 to about 12 cP, at a jetting temperature of from about 60 to about 125° C. such as from about 80 to about 125° C., for example from about 100 to about 120° C. High energy inks are solid at a temperature below 40° C. and have a viscosity of from about 5 to about 15 cP at a jetting temperature of from about 100 to about 180° C., for example from about 120 to about 160° C. or from about 125 to about 150° C.

The term "ink vehicle" generally refers to the material which carries the dispersant coated pigment particles. Any suitable ink vehicle can be employed, so long as the ink vehicle is non-aqueous. For example, the ink vehicle can be a wax or a non-polar solvent. Suitable vehicles can include paraffins, microcrystalline waxes, polyethylene waxes, ester waxes, amides, long chain acids with at least about 30 carbons, fatty acids and other waxy materials, fatty amide containing materials, sulfonamide materials, resinous materials made from different natural sources (tall oil rosins and rosin esters, for example), and many synthetic resins, oligomers, polymers, and copolymers such as those further discussed below.

Examples of suitable amides include, for example, diamides, triamides, tetra-amides, cyclic amides and the like.

Other suitable vehicle materials that can be used in the solid ink compositions include, for example, isocyanate-derived resins and waxes, such as urethane isocyanate-derived materials, urea isocyanate-derived materials, urethane/urea isocyanate-derived materials, mixtures thereof, and the like.

Examples of suitable ink vehicles include, for example, ethylene/propylene copolymers, such as those available from Baker Petrolite. Commercial examples of such copolymers include, for example, Petrolite CP-7 (Mn=650), Petrolite CP-11 (Mn=1,100, Petrolite CP-12 (Mn=1,200) and the like. The copolymers may have, for example, a melting point of from about 70° C. to about 150° C., such as from about 80° C.

to about 130° C. or from about 90° C. to about 120° C. and a molecular weight range (Mn) of from about 500 to about 4,000.

Urethane derivatives of oxidized synthetic or petroleum waxes, such as those available from Baker Petrolite and of the general formulas

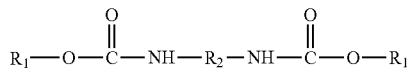

wherein $R_1$ is an alkyl group of the formula $CH_3(CH_2)_n$, n is an integer of from about 5 to about 200, for example from about 10 to about 150 or from about 10 to about 100 and $R_2$ is an arylene group, may also be used as the ink vehicle. These materials may have a melting point of from about 60° C. to about 120° C., such as from about 70° C. to about 100° C. or from about 70° C. to about 90° C. Commercial examples of such materials include, for example, Baker Petrolite CA-11 (Mn=790, Mw/Mn=2.2), Petrolite WB-5 (Mn=650, Mw/Mn=1.7), Petrolite WB-17 (Mn=730, Mw/Mn=1.8), and the like.

Another type of ink vehicle may be n-paraffinic, branched paraffinic, and/or naphthenic hydrocarbons, typically with from about 5 to about 100, such as from about 20 to about 80 or from about 30 to about 60 carbon atoms, generally prepared by the refinement of naturally occurring hydrocarbons, such as BE SQUARE® 185 and BE SQUARE® 195, with number average molecular weights (Mn) of from about 100 to about 5,000, such as from about 250 to about 1,000 or from about 500 to about 800, for example such as available from Baker Petrolite.

Highly branched hydrocarbons, typically prepared by olefin polymerization, such as the VYBAR® materials available from Baker Petrolite, including VYBAR® 253 (Mn=520), VYBAR® 5013 (Mn=420), and the like, may also be used. In addition, the ink vehicle may be an ethoxylated alcohol, such as available from Baker Petrolite and of the general formula

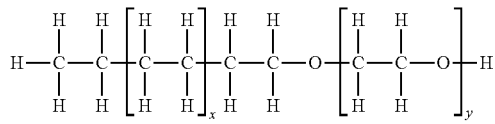

wherein x is an integer of from about 1 to about 50, such as from about 5 to about 40 or from about 11 to about 24 and y is an integer of from about 1 to about 70, such as from about 1 to about 50 or from about 1 to about 40. The materials may have a melting point of from about 60 to about 150° C., such as from about 70 to about 120° C. or from about 80 to about 110° C. and a number-average molecular weight (Mn) range of from about 100 to about 5,000, such as from about 500 to about 3,000 or from about 500 to about 2,500. Commercial examples include UNITHOX® 420 (Mn=560), UNITHOX® 450 (Mn=900), UNITHOX® 480 (Mn=2,250), UNITHOX® 520 (Mn=700), UNITHOX® 550 (Mn=1,100), UNITHOX® 720 (Mn=875), UNITHOX® 750 (Mn=1,400), and the like.

As an additional example, the ink vehicle may be made of fatty amides, such as monoamides, tetra-amides, mixtures thereof, and the like, for example such as described in U.S. Pat. No. 6,858,070, which is hereby incorporated by reference herein in its entirety. Suitable monoamides may have a melting point of at least about 50° C., for example from about 50° C. to about 150° C., although the melting point can be outside these ranges. Specific examples of suitable monoamides include, for example, primary monoamides and secondary monoamides. Stearamide, such as KEMAMIDE® S available from Witco Chemical Company and CRODAMIDE® S available from Croda, behenamide/arachidamide, such as KEMAMIDE® B available from Witco and CRODAMIDE® BR available from Croda, oleamide, such as KEMAMIDE® U available from Witco and CRODAMIDE® OR available from Croda, technical grade oleamide, such as KEMAMIDE® O available from Witco, CRODAMIDE® O available from Croda, and UNISLIP® 1753 available from Uniqema, and erucamide such as KEMAMIDE® E available from Witco and CRODAMIDE® ER available from Croda, are some examples of suitable primary amides. Behenyl behenamide, such as KEMAMIDE EX666 available from Witco, stearyl stearamide, such as KEMAMIDE® S-180 and KEMAMIDE® EX-672 available from Witco, stearyl erucamide, such as KEMAMIDE® E-180 available from Witco and CRODAMIDE® 212 available from Croda, erucyl erucamide, such as KEMAMIDE® E-221 available from Witco, oleyl palmitamide, such as KEMAMIDE® P-181 available from Witco and CRODAMIDE® 203 available from Croda, and erucyl stearamide, such as KEMAMIDE® S-221 available from Witco, are some examples of suitable secondary amides. Additional suitable amide materials include KEMAMIDE® W40 (N,N'-ethylenebisstearamide), KEMAMIDE® P181 (oleyl palmitamide), KEMAMIDE® W45 (N,N'-thylenebisstearamide), and KEMAMIDE® W20 (N,N'-ethylenebisoleamide).

High molecular weight linear alcohols, such as those available from Baker Petrolite and of the general formula

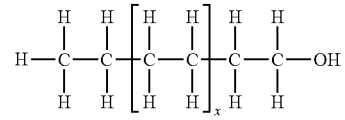

wherein x is an integer of from about 1 to about 50, such as from about 5 to about 35 or from about 11 to about 23, may also be used as the ink vehicle. These materials may have a melting point of from about 50 to about 150° C., such as from about 70 to about 120° C. or from about 75 to about 110° C., and a number-average molecular weight (Mn) range of from about 100 to about 5,000, such as from about 200 to about 2,500 or from about 300 to about 1,500. Commercial examples include the UNILIN® materials such as UNILIN® 425 (Mn=460), UNILIN® 550 (Mn=550), UNILIN® 700 (Mn=700), and distilled alcohols, the viscosity of which at the jetting temperature in one embodiment can be from about 5 to about 50% higher than the non-distilled alcohol.

A still further example includes hydrocarbon-based waxes, such as the homopolymers of polyethylene available from Baker Petrolite and of the general formula

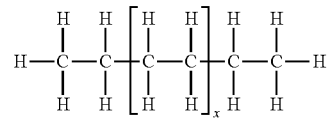

wherein x is an integer of from about 1 to about 200, such as from about 5 to about 150 or from about 12 to about 105. These materials may have a melting point of from about 60° C. to about 150° C., such as from about 70° C. to about 140°

C. or from about 80° C. to about 130° C. and a molecular weight (Mn) of from about 100 to about 5,000, such as from about 200 to about 4,000 or from about 400 to about 3,000. Example waxes include PW400 (Mn about 400), distilled PW400, in one embodiment having a viscosity of about 10% to about 100% higher than the viscosity of the undistilled POLYWAX® 400 at about 110° C., POLYWAX 500 (Mn about 500), distilled POLYWAX® 500, in one embodiment having a viscosity of about 10% to about 100% higher than the viscosity of the undistilled POLYWAX® 500 at about 110° C., POLYWAX 655 (Mn about 655), distilled POLYWAX® 655, in one embodiment having a viscosity of about 10% to about 50% lower than the viscosity of the undistilled POLYWAX® 655 at about 110° C., and in yet another embodiment having a viscosity of about 10% to about 50% higher than the viscosity of the undistilled POLYWAX® 655 at about 110° C. POLYWAX® 850 (Mn about 850), POLYWAX® 1000 (Mn about 1,000), and the like.

Another example includes modified maleic anhydride hydrocarbon adducts of polyolefins prepared by graft copolymerization, such as those available from Baker Petrolite and of the general formulas

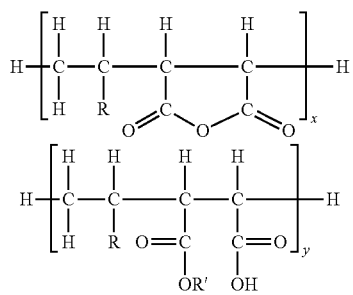

wherein R is an alkyl group with from about 1 to about 50, such as from about 5 to about 35 or from about 6 to about 28 carbon atoms, R' is an ethyl group, a propyl group, an isopropyl group, a butyl group, an isobutyl group, or an alkyl group with from about 5 to about 500, such as from about 10 to about 300 or from about 20 to about 200 carbon atoms, x is an integer of from about 9 to about 13, and y is an integer of from about 1 to about 50, such as from about 5 to about 25 or from about 9 to about 13, and having melting points of from about 50 to about 150° C., such as from about 60 to about 120° C. or from about 70 to about 100° C.; and those available from Baker Petrolite and of the general formula

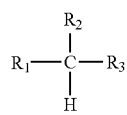

wherein $R_1$ and $R_3$ are hydrocarbon groups and $R_2$ is either of one of the general formulas

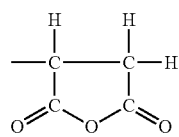

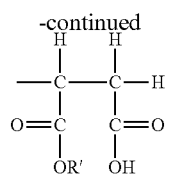

or a mixture thereof, wherein R' is an isopropyl group, which materials may have melting points of from about 70° C. to about 150° C., such as from about 80° C. to about 130° C. or from about 90° C. to about 125° C., with examples of modified maleic anhydride copolymers including CERAMER® 67 (Mn=655, Mw/Mn=1.1), CERAMER® 1608 (Mn=700, Mw/Mn=1.7), and the like.

Additional examples of suitable ink vehicles for the phase change inks include rosin esters; polyamides; dimer acid amides; fatty acid amides, including ARAMID® C; epoxy resins, such as EPOTUF® 37001, available from Riechold Chemical Company; fluid paraffin waxes; fluid microcrystalline waxes; Fischer-Tropsch waxes; polyvinyl alcohol resins; polyols; cellulose esters; cellulose ethers; polyvinyl pyridine resins; fatty acids; fatty acid esters; poly sulfonamides, including KETJENFLEX® MH and KETJENFLEX® MS80; benzoate esters, such as BENZOFLEX® 5552, available from Velsicol Chemical Company; phthalate plasticizers; citrate plasticizers; maleate plasticizers; sulfones, such as diphenyl sulfone, n-decyl sulfone, n-amyl sulfone, chlorophenyl methyl sulfone; polyvinyl pyrrolidinone copolymers; polyvinyl pyrrolidone/polyvinyl acetate copolymers; novolac resins, such as DUREZ® 12 686, available from Occidental Chemical Company; and natural product waxes, such as beeswax, monton wax, candelilla wax, GILSONITE® (American Gilsonite Company), and the like; mixtures of linear primary alcohols with linear long chain amides or fatty acid amides, such as those with from about 6 to about 24 carbon atoms, including PARICIN® 9 (propylene glycol monohydroxystearate), PARICIN® 13 (glycerol monohydroxystearate), PARICIN® 15 (ethylene glycol monohydroxystearate), PARICIN® 220 (N(2-hydroxyethyl)-12-hydroxystearamide), PARICIN® 285 (N,N'-ethylene-bis-12-hydroxystearamide), FLEXRICIN® 185 (N,N'-ethylene-bis-ricinoleamide), and the like. Further, linear long chain sulfones with from about 4 to about 16 carbon atoms, such as n-propyl sulfone, n-pentyl sulfone, n-hexyl sulfone, n-heptyl sulfone, n-octyl sulfone, n-nonyl sulfone, n-decyl sulfone, n-undecyl sulfone, n-dodecyl sulfone, n-tridecyl sulfone, n-tetradecyl sulfone, n-pentadecyl sulfone, n-hexadecyl sulfone, and the like, are suitable ink vehicle materials.

In addition, the ink vehicles described in U.S. Pat. No. 6,906,118, which is totally incorporated herein by reference, may also be used. The ink vehicle may contain a branched triamide such as those described in U.S. Pat. No. 6,860,930, the disclosure of which is totally included here by reference, such as

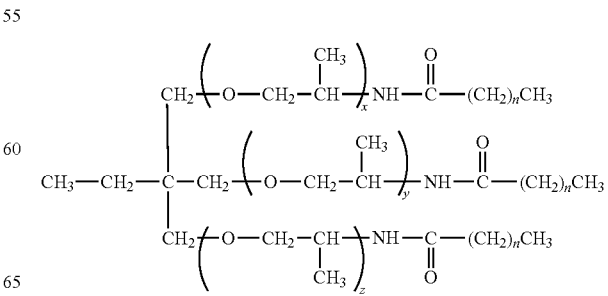

wherein n has an average value of from about 34 equal to or less than 40, where x, y and z can each be zero or an integer, and wherein the sum of x, y, and z is from about 5 and equal to or less than 6.

The ink vehicle may comprise one or more of the aforementioned suitable materials.

The ink vehicles for the phase change inks may have melting points of from about 60 to about 150° C., for example from about 80 to about 120° C. or from about 85 to about 110° C., as determined by, for example, observation and measurement on a microscope hot stage, wherein the binder material is heated on a glass slide and observed by microscope. Higher melting points are also acceptable, although printhead life may be reduced at temperatures higher than 150° C.

In addition, the surface tension of the ink at the operating (jetting) temperature of the ink should be from about 20 to about 40 dynes per centimeter, for example from about 40 to about 65 dynes per centimeter, to enhance refill rates and color mixing. The operating, or jetting, temperatures of the phase change inks generally are from about 60 to about 150° C. The viscosity of the ink at the operating temperature of the ink is generally from about 1 to about 20 cP, for example from about 1 to about 15 cP or from about 5 to about 15 cP.

The ink composition as a whole generally includes the ink vehicle (that is, exclusive of pigment particles, and the like) in an amount of from about 25% to about 99.5% by weight of the ink, for example from about 30% to about 90% or from about 50% to about 85% by weight of the ink.

The phase change inks of the disclosure contain at least one pigment. The pigment is present in the ink in any desired amount, typically from about 0.5 to about 30 percent by weight of the ink vehicle or ink vehicle/propellant mixture, for example from about 1 to about 50 percent by weight of the ink vehicle or ink vehicle/propellant mixture. In one embodiment, the ink may contain a mixture of at least two different pigments.

Examples of suitable pigments include, but are not limited to, Violet Paliogen Violet 5100 (BASF); Paliogen Violet 5890 (BASF); Heliogen Green L8730 (BASF); Lithol Scarlet D3700 (BASF); Sunfast® Blue 15:4 (Sun Chemical 249-0592); Hostaperm Blue B4-G (Clariant); Hostaperm Blue B2G-D (Clariant); Permanent Red P-F7RK; Hostaperm Violet BL (Clariant); Lithol Scarlet 4440 (BASF); Bon Red C (Dominion Color Company); Oracet Pink RF (Ciba); Paliogen Red 3871 K (BASF); Sunfast® Blue 15:3 (Sun Chemical 249-1284); Paliogen Red 3340 (BASF); Sunfast® Carbazole Violet 23 (Sun Chemical 246-1670); Lithol Fast Scarlet L4300 (BASF); Sunbrite Yellow 17 (Sun Chemical 275-0023); Heliogen Blue L6900, L7020 (BASF); Sunbrite Yellow 74 (Sun Chemical 272-0558); Spectra Pac® C Orange 16 (Sun Chemical 276-3016); Heliogen Blue K6902, K6910 (BASF); Sunfast® Magenta 122 (Sun Chemical 228-0013); Heliogen Blue D6840, D7080 (BASF); Sudan Blue OS (BASF); Neopen Blue FF4012 (BASF); PV Fast Blue B2GO1 (Clariant); Irgalite Blue BCA (Ciba); Paliogen Blue 6470 (BASF); Sudan Orange G (Aldrich), Sudan Orange 220 (BASF); Paliogen Orange 3040 (BASF); Paliogen Yellow 152, 1560 (BASF); Lithol Fast Yellow 0991 K (BASF); Paliotol Yellow 1840 (BASF); Novoperm Yellow FGL (Clariant); Lumogen Yellow D0790 (BASF); Suco-Yellow L1250 (BASF); Suco-Yellow D1355 (BASF); Suco Fast Yellow D1355, D1351 (BASF); Hostaperm Pink E 02 (Clariant); Hansa Brilliant Yellow 5GX03 (Clariant); Permanent Yellow GRL 02 (Clariant); Permanent Rubine L6B 05 (Clariant); Fanal Pink D4830 (BASF); Cinquasia Magenta (Du Pont); Paliogen Black L0084 (BASF); Pigment Black K801 (BASF); and carbon blacks such as REGAL 330™ (Cabot), Carbon Black 5250, Carbon Black 5750 (Columbia Chemical), mixtures thereof and the like.

In some embodiments, the pigment is a magenta pigment such as pigment red 57.1 pigment. Suitable magenta pigments include those that have a primary average particle size range from about 50 to about 200 nm as determined by transmission electron microscopy according to ASTM 3849, more preferably a particle size range of 50 to 150 nm. The average primary particle size indicates the size of the primary particles of pigment present in the ink; these primary particles may form aggregates of two or more particles when present in the ink. In other embodiments, the pigment is a yellow pigment such as pigment yellow 155, pigment yellow 180, or pigment yellow 139.

Optionally, a propellant may be contained in the phase change ink, although it is not required in many ink compositions. Suitable propellants for the phase change inks, present in any effective amount such as from about 10 to about 90 percent by weight, for example from about 20 to about 50 percent by weight, of the ink generally have melting points of from about 50 to about 150° C., for example from about 80 to about 120° C. In another embodiment, the propellants generally have a boiling point of from about 180 to about 250° C., for example from about 200 to about 230° C. Further, the surface tension of the propellant in its liquid state at the operating temperature of the ink may be from about 20 to about 65 dynes per centimeter, for example from about 40 to about 65 dynes per centimeter, to enhance refill rates, paper wetting, and color mixing. In addition, the propellants ideally have a viscosity at the operating temperature of the ink of from about 1 to about 20 centipoise, for example from about 1 to about 5 centipoise, to enhance refill and jettability. The propellant may also be thermally stable in its molten state so that it does not undergo decomposition to yield gaseous products or to form heater deposits.

The ink can also contain an antioxidant. The antioxidants of the ink compositions protect the ink components from oxidation during the heating portion of the ink preparation and jetting processes. Specific examples of suitable antioxidants are set forth in U.S. Pat. No. 6,858,070, the disclosure of which is totally incorporated herein by reference. When present, the optional antioxidant is present in the ink in any desired or effective amount, in one embodiment of at least about 0.01% by weight of the ink vehicle, in another embodiment of at least about 0.1% by weight of the ink vehicle, and in yet another embodiment of at least about 1% by weight of the ink vehicle, and in one embodiment of equal to or less than about 20% by weight of the ink vehicle, in another embodiment equal to or less than about 5% by weight of the ink vehicle, and in yet another embodiment equal to or less than about 3% by weight of the ink vehicle, although the amount can be outside of these ranges. When only one antioxidant is used, a hindered amine is preferred, e.g.: Naugard® 445 antioxidant (obtained from Uniroyal Chemical Co., Middlebury, Conn. or Crompton Corporation) In other embodiments, mixtures of antioxidants used to improve melt processing stability and long-term thermal stability include, but are not limited to, hindered amines, phosphites, hindered phenols, hydroxylamines, lactones, tocopherols, thiosynergists, and the like.

The ink disclosed herein can also contain resins and waxes such as: Crodamide® 203 (commercially available from Croda), Crodamide® ORX (commercially available from Croda), Kemamide® S-180 and E-180 (commercially available from Witco), Unislip 1750 (commercially available from Uniqema), Uniclear® 80 (commercially available from Arizona), a dicaprylapidate compatibilizer such as Arizona SP-100, Vybar® 263 and 243 (commercially available from Baker Petrolite), 1-docosanol (commercially available from Aldrich), Unilin® 700 (commercially available from Baker Hughes), Beeswax Cerra Bellina® (commercially available from Kester Keunen), branched BK-42 ester (commercially available from Kester Keunen), Kester Wax® K82-D, hydroxypolyester K-82-P, synthetic Karnauba K-82-H, Siliconyl Beeswax (commercially available from Kester Keunen), stearyl alcohol 98 NF (commercially available from Kester Keunen), Kraton D1101 (commercially available from Kraton Polymers), Behenyl Behenate, straight chain even numbered mono esters having a carbon chain from C-40 to C44 (commercially available from Kester Keunen as Kester Wax® 72), synthetic paraffin wax of a sharp melting point such as Callista® 158 (commercially available from Shell), microcrystalline branched hydrocarbon waxes such as Microwax® HG (commercially available from Paramelt), Mp=80-86, and Microwax® P827, Kemamide® 5-221, polyethyleneglycol 400 distearate (commercially available from Mosselman); paraffin waxes such as HNP-9 and HNP-12 (commercially available from Nippon Seiro Co.); semi-crystalline wax such as HIMIC-2065® (commercially available from Nippon Seiro Co.); hydrogenated styrene-butadiene copolymers of low molecular weight such as Tuftec® H1141.11102 (commercially available from Asahi Kasei Corp); ethylene-propylene copolymers such as EP-700® and EP-602® (commercially available from Baker Hughes); Unithox 420® ethoxylate (commercially available from Baker Hughes); propylene-ethylene copolymer alcohols of melting point in the range of 65 to 100° C. (commercially available from Baker Hughes); maleic anhydride mono-isopropyl maleate such as Ceramer 1251 (commercially available from Baker Hughes); alpha olefin-maleic anhydride polymer of melting point of about 80 degree C. (commercially available from Baker Petrolite) (X-5399); oxidized ethene homopolymer, Petrolite C-9500 (commercially available from Baker Hughes); oxidized 1-propene with ethane, Cardis® 314, (commercially available from Baker Hughes), Victory Amber wax (commercially available from Bareco), oxidized PE such as OX-020T (commercially available from Nippon Seiro Co.). The ink can also contain paraffin waxes and microcrystalline waxes. Paraffin wax is a straight chain hydrocarbon having a melting point of about 49 to 71 degree C.; microcrystalline wax is separated from asphalts and is higher in MW and more branched than the paraffin wax. The melting point of microcrystalline waxes is between 60 and 89° C. Examples of suitable paraffin waxes are HNP-3, 5, 9, 10, 11 and HNP-12 (commercially available from Nippon Seiro Co.).

The inks of embodiments may further include conventional additives to take advantage of the known functionality associated with such conventional additives. Such additives may include, for example, defoamers, slip and leveling agents, plasticizers, pigment dispersants, etc.

Other optional additives such as plasticizers may be present in the inks. Plasticizers that may be used include pentaerythritol tetrabenzoate, commercially available as BENZOFLEX® S552 (Velsicol Chemical Corporation), trimethyl titrate, commercially available as CITROFLEX® 1 (Monflex Chemical Company), N,N-dimethyl oleamide, commercially available as HALCOMID® M-18-OL (C. P. Hall Company), and the like, may be added to the ink vehicle, and may constitute from about 0.5 to 20 percent of the ink vehicle component of the ink. Plasticizers can either function as the ink vehicle or can act as an agent to provide compatibility between the ink propellant, which generally is polar, and the ink vehicle, which generally is non-polar.

Preparation of Pigmented Phase Change Ink Compositions can include the partial or total inclusion of ink components therein during the act of pigment dispersion making. This can also include the dispersing of pigment at various pigment concentrations at various temperatures with various inputted energies. The pigment can be processed, with or without at least one dispersant, such that it is dispersed by various means including ball mills, attritors, Cobol mills, Dyno mills, paint shakers, pearl mills, agitator mills, two-roll mills, high speed stirring, three-roll mills, flow jet mills, extruders, homogenizers, kneaders and the like.

The pigment can be optionally processed with suitable grinding media in any of the aforementioned dispersing equipment, where it is applicable, such as steel balls, glass balls, glass beads, polyethylene beads, Nylon beads, ceramic beads and the like. The phase change ink compositions may be prepared by combining some or all of the components, heating the mixture to at least its melting point, for example from about 70 to about 120° C., and stirring the mixture, until a substantially homogeneous and uniform melt is obtained. For example, the molten mixture may be subjected to grinding in an attritor or ball mill apparatus to effect dispersion of the pigment in the ink vehicle.

The phase change ink can also be prepared by first admixing in an extruder the pigment together with the dispersant, or part of the ink ingredients in an extruder, at the optimum process conditions to shear and wet the pigment. The resulting pigment dispersion should have a viscosity sufficiently low to enable mixing in the extruder, and also sufficiently high to enable a desirable degree of shear to be generated within the extruder. Any desired or effective extruder can be employed, including single screw extruders, twin screw extruders, including co-rotating twin screw extruders (wherein both screws rotate in the same direction), counter-rotating twin screw extruders (wherein the screws rotate in opposite directions), and the like. Admixing the resulting pigment dispersion with the additional ink carrier ingredients and any desired additional optional ingredients and subjecting the resulting mixture to high shear agitation using the equipments as mentioned above to prepare the ink.

Printed images may be generated with the inks described herein by incorporating one or more of the solid inks into a printer that is used in an ink jet device, for example a thermal ink jet device, an acoustic ink jet device or a piezoelectric ink jet device, and concurrently causing droplets of the inks to be ejected in an imagewise pattern onto an image receiving substrate such as paper or transparency material. Each ink of the ink sets is typically included in a reservoir connected by any suitable feeding device to the corresponding ejecting channels of the ink jet head. In the jetting procedure, the ink jet head may be heated, by any suitable method, to the jetting temperature of the inks.

The inks can also be employed in indirect printing ink jet applications, wherein when droplets of the melted ink are ejected in an imagewise pattern onto an image receiving substrate, the substrate is an intermediate transfer member and the ink in the imagewise pattern is subsequently transferred from the intermediate transfer member to a final recording substrate. The intermediate transfer member may be, for example, a drum.

In embodiments using an intermediate transfer member, the member may be heated to have a temperature on a surface thereof of from about 45 to about 80° C. The elevated surface temperature permits the ink to remain in a molten state while avoiding offset or ink splitting on the surface of the transfer member, thereby enabling good transfer of the image to the end image receiving substrate such as paper or transparency.

In embodiments, the ink jet system thus includes the aforementioned inks in an ink set comprised of at least three differently colored phase change inks, such as cyan, magenta, yellow and black inks. The system also includes an ink jet device including an ink jet head consisting of one channel for each one of the differently colored phase change inks in the ink set, and a supply path that supplies each of the differently colored phase change inks to the respective channels of the ink jet head, for example from reservoirs containing each of the differently colored phase change inks.

Any suitable substrate or recording sheet can be employed, including plain papers such as XEROX® 4200 papers XEROX® 4024 papers, XEROX® Image Series papers, Courtland 4024 DP paper, ruled notebook paper, bond paper, silica coated papers such as Sharp Company silica coated paper, JuJo paper, Hammermill Laserprint Paper, and the like, transparency materials, fabrics, textile products, plastics, polymeric films, inorganic substrates such as metals and wood, and the like.

It is desirable that the pigmented ink have certain attributes that include having good filterability, remain stable over several successive freeze thaw cycles, and have good rheological stability for at least 10 days at 120° C. In further embodiments, the pigmented inks have good filterability, remain stable over several successive free/thaw cycles, and have good rheological stability for at least 17, at least 18, or at least 39 days at 120° C. Furthermore, the inks do not show any significant settling after 7 days at 120° C., or after 14 days at 120° C. The disclosed inks, in embodiments, exhibit Newtonian rheology properties, in addition to improved stability. The disclosed pigmented inks can be printed over a temperature range of about 100° C. to about 150° C., however, it is advantageous to print at relatively lower temperatures to further reduce printing costs by reducing energy consumption. These properties indicate that the inks include well-dispersed pigment particles with no evidence of pigment particle flocculation and settling. The pigmented ink stability is monitored using any number of suitable Dynamic Light Scattering apparatuses, such as a Malvern Zetasizer. For instance, the Z-average particle size over time can be monitored to gauge the stability of the pigment particles in the ink while it is held at elevated temperatures, such as about 120° C.

EXAMPLES

The following Examples are being submitted to further define various species of the present disclosure. These Examples are intended to be illustrative only and are not intended to limit the scope of the present disclosure. Also, parts and percentages are by weight unless otherwise indicated.

TABLE 1

| | Dispersants | | |
|---|---|---|---|
| Example | Carboxylic Acid Brush Length (Average Number of Carbon Atoms) | Amine/Mn | Ratio Acid:Amine |
| 1 | C48 | ethylenimine/250-300 | 1:1 |
| 2 | C48 | ethylenimine/250-300 | 2:1 |
| 3 | C48 | polyethylenimine/423 | 1:1 |
| 4 | C48 | polyethylenimine/423 | 2:1 |
| 5 | C30 | polyethylenimine/423 | 2:1 |
| 6 | C38 | polyethylenimine/423 | 2:1 |
| 7 | C22 | polyethylenimine/423 | 2:1 |
| 8 | C48 | polyethylenimine/600 | 1:1 |

TABLE 1-continued

| | Dispersants | | |
|---|---|---|---|
| Example | Carboxylic Acid Brush Length (Average Number of Carbon Atoms) | Amine/Mn | Ratio Acid:Amine |
| 9 | C48 | polyethylenimine/600 | 2:1 |
| 10 | C48 | ethylene diamine | 1:1 |
| 11 | C48 | ethylene diamine | 2:1 |
| 12 | C48 | ethylene triamine | 1:1 |
| 13 | C48 | ethylene triamine | 2:1 |
| 14 | C48 | tetraethylene pentaamine | 1:1 |
| 15 | C48 | tetraethylene pentaamine | 2:1 |
| 16 | C48 | tetraethylene pentaamine | 1.5:1 |
| 17 | C48 | Ethyleneimine/250-300 | 1.5:1 |

Examples 1-17 having dispersants as described in Table 1 were synthesized as follows.

Example 1

Into a 1 liter resin kettle fitted with heating mantle, mechanical stirring, Dean-Stark trap, reflux condenser and temperature sensor were introduced 192.78 grams (g) of Unicid® 700 (a long chain, linear carboxylic acid having an average carbon chain length of 48, available from Baker Petrolite) and 60.3 g of E-100® (a mixture of tetraethylenepentamine, (TEPA), pentaethylenehexamine (PEHA), hexaethyleneheptamine (HEHA), and higher molecular weight materials with a number-average molecular weight of 250 to 300 grams per mole, available from Huntsman. Under a stream of Argon, the temperature in the kettle was raised to 100° C. and the resin was allowed to melt. When the resin was completely melted, the temperature was gradually raised to 180° C. with stirring, and the reaction was allowed to proceed for 3 hours. 3.6 milliliters of water was collected into the Dean-Stark trap. The reaction was stopped, cooled down to 140° C. and discharged to an aluminum tray to give 249 g of the amide as a beige solid.

Example 2

Into a 1 liter resin kettle fitted with heating mantle, mechanical stirring, Dean-Stark trap, reflux condenser and temperature sensor were introduced 337.0 g of Unicid® 700 and 103.3 g E-100®. Under a stream of Argon, the temperature in the kettle was raised to 100° C. and the resin was allowed to melt. When the resin was completely melted, the temperature was gradually raised to 180° C. with stirring, and the reaction was allowed to proceed for 3 hours. 6 milliliters of water was collected into the Dean-Stark trap. The reaction was stopped, cooled down to 140° C. and discharged into an aluminum tray to give 378 g of the amide as a beige solid.

Example 3

Into a 1 liter resin kettle fitted with heating mantle, mechanical stirring, Dean-Stark trap, reflux condenser and temperature sensor were introduced 250.0 g of Unicid® 700 and 103.3 g of polyethylenimine (Aldrich, Mn about 423). Under a stream of Argon, the temperature in the kettle was raised to 90° C. and the resin was allowed to melt. When the resin was completely melted, the temperature was gradually raised to 180° C. with stirring, and the reaction was allowed to proceed for 2.5 hours. 3.9 milliliters of water was collected into the Dean-Stark trap. The reaction was stopped, cooled down to 140° C. and discharged into an aluminum tray to give 333 g of the amide as a light brown solid.

Example 4

Dispersant Example 4 was prepared using the same procedure outlined for Dispersant Example 3 except a 2:1 ratio of Unicid® 700 to polyethyleneimine was used in place of the 1:1 ratio used in Example 3. For Example 4, 250 g of Unicid 700® and 54.8 g of polyethylenimine having a Mn of about 423 were used. 278 g of a light brown solid product was obtained.

Example 5

Dispersant Example 5 was prepared using the same procedure outlined for Dispersant Example 3 except Unicid® 425 (a long chain, linear carboxylic acid having an average carbon chain length of 30, available from Baker Petrolite) was used in place of Unicid® 700 and a 2:1 ratio of Unicid® 425 to polyethylenimine was used. For Example 5, 178.56 g of Unicid® 425 and 53.72 g of polyethylenimine having a Mn of about 423 were used. 227.7 g of a light brown solid product was obtained.

Example 6

Dispersant Example 6 was prepared using the same procedure outlined for Dispersant Example 3 except Unicid® 550 (a long chain, linear carboxylic acid having an average carbon chain length of 38, available from Baker Petrolite) was used in place of Unicid® 700 and a 2:1 ratio of Unicid® 550 to polyethylenimine was used. For Example 6, 160.38 g of Unicid® 550 and 42.30 g of polyethylenimine having a Mn of about 423 were used. 199.08 g of a light brown solid product was obtained.

Example 7

Dispersant Example 7 was prepared using the same procedure outlined for Dispersant Example 3 except Behenic acid (a long chain, linear carboxylic acid having an average carbon chain length of 22, available from Kester Keunen, Watertown, Conn.) was used in place of Unicid® 700 and a 2:1 ratio of Behenic acid to polyethylenimine was used. For Example 7, 81.51 g of Behenic acid and 57.22 g of polyethylenimine having a Mn of about 423 were used. 135 g of a light brown solid product was obtained.

Example 8

Dispersant Example 8 was prepared using the same procedure outlined for Dispersant Example 3 except polyethylenimine having a Mn of 600 was used. For Example 8, 150.27 g of Unicid® 700 and 90.0 g of polyethylenimine (Aldrich, Mn about 600) were used. 237.57 g of a light brown solid product were obtained.

Example 9

Dispersant Example 9 was prepared using the same procedure outlined for Dispersant Example 3 except polyethylenimine having a Mn of about 600 was used with a 2:1 ratio of Unicid® 700 to polyethylenimine. For Example 9, 150.27 g of Unicid® 700 and 45.0 g of polyethylenimine (Aldrich, Mn about 600) were used. 192.57 g of a light brown solid product was obtained.

Example 10

Dispersant Example 10 was prepared as follows. Into a 1 liter resin kettle fitted with mechanical stirring, heating mantle, temperature controller, Argon inlet, Dean-Stark trap and reflux condenser were introduced 144.6 g of Unicid® 700 and 9.02 g of ethylene diamine (Aldrich) in a 1:1 ratio of acid to amine. Under a stream of Argon, the temperature in the kettle was raised to 100° C. and the Unicid® 700 resin was allowed to melt. When the reaction mixture was homogenous (that is, when the Unicid® 700 has completely melted), the temperature was gradually raised to 180° C. with stirring, and the reaction was allowed to proceed for 3 to 5 hours depending on titration results. 3 ml of water was collected into the Dean-Stark trap. When the acid number remained constant, the reaction was stopped, cooled down to 150° C. and the product discharged into an aluminum tray to give 146 g of the amide product as a light brown solid.

Example 11

Dispersant Example 11 was prepared using the same procedure outlined for Dispersant Example 10 except that a 2:1 ratio of acid to amine was used. For Example 11, 260.26 g of Unicid® 700 and 81.2 g of ethylene diamine were used. 247 g of a light brown solid amide product was obtained.

Example 12

Dispersant Example 12 was prepared using the same procedure outlined for Dispersant Example 10 except that ethylene triamine (Aldrich) was used in a 1:1 ratio of acid to amine. For Example 12, 144.6 g of Unicid® 700 and 15.48 g of ethylene triamine were used. 146 g of a light brown solid amide product was obtained.

Example 13

Dispersant Example 13 was prepared using the same procedure outlined for Dispersant Example 10 except that ethylene triamine (Aldrich) was used in a 2:1 ratio of acid to amine For Example 13, 240.98 g of Unicid® 700 and 12.9 g of ethylene triamine were used. 246 g of a light brown solid amide product was obtained.

Example 14

Dispersant Example 14 was prepared using the same procedure outlined for Dispersant Example 10 except that tetraethylene pentaamine (TEPA, Huntsman) was used in a 1:1 ratio of acid to amine. For Example 14, 337.37 g of Unicid® 700 and 33.08 g of tetraethylene pentaamine were used. 352 g of a light brown solid amide product was obtained.

Example 15

Dispersant Example 15 was prepared using the same procedure outlined for Dispersant Example 10 except that tetraethylene pentaamine (TEPA, Huntsman) was used in a 2:1 ratio of acid to amine. For Example 15, 308.45 g of Unicid® 700 and 60.48 g of tetraethylene pentaamine were used. 352 g of a light brown solid amide product was obtained.

The compounds were characterized through differential scanning calorimetry (DSC), infrared spectroscopy (IR), and titration (acid number and amine number). The reaction was followed by titration, samples were taken, and acid and amine number were measured hourly to assess completion. When the acid number remained constant even after several hours of heating at 180° C., the reaction was judged as complete. The characterization results for DSC and titration are presented in Table 2.

Example 16

Dispersant Example 16 was prepared using the same procedure outlined for Dispersant Example 10 except that tetraethylene pentaamine (TEPA, Huntsman) was used in a 1.5:1 ratio of acid to amine For Example 16, 173.51 g of Unicid® 700 and 22.68 g of tetraethylene pentaamine were used. 187 g of a light brown solid amide product was obtained.

Example 17

Dispersant Example 17 was prepared using the same procedure outlined for Dispersant Example 10 except that a 1.5:1 ratio of acid to amine was used. For Example 17, 173.51 g of Unicid® 700 and 36 g ethylene imine E-100® were used. 200 g of a light brown solid amide product was obtained.

TABLE 2

Dispersant Characterization

| Dispersant Example | Titration | | DSC | | | |
|---|---|---|---|---|---|---|
| | Acid # | Amine # | Onset of Crystallization (° C.) | Peak of Crystallization (° C.) | Peak of Melting (° C.) | End of Melting (° C.) |
| 1 | 0.87 | >100 | 97.6 | 94.4 | 102.1 (92.6) | 105.2 |
| 2 | 1.55 | 83.27 | 96.7 | 94.3 | 106.9 | 108.7 |
| 3 | 1.14 | >250 | 96 | 93.8 | 102.2 | 106.7 |
| 4 | 0.98 | 128 | 99.6 | 97.2 | 104.1 | 107.3 |
| 5 | 1.06 | 188 | 82.7 | 79.3 | 76.01 | 96.9 |
| 6 | 1.19 | >150 | 92.4 | 89.4 | 96.6 | 104.1 |
| 7 | 1.75 | >150 | 63.1 | (53.5) 59.7 | (56.3) 65.8 | 72.9 |
| 8 | 1.22 | >150 | 93.3 | 91 | 102 | 106.4 |
| 9 | 1.14 | 153 | 93 | 90.9 | 101.7 | 106.1 |
| 10 | 10.8 | 8.05 | 121.0 | 120.7 (101.4) | 123.7 (102.3) | 123 |
| 11 | 11.15 | 3.81 | 120.5 | 119.7 (96.7) | 123.6 (101.9) | 126.0 |
| 12 | 2.35 | 45.3 | 98.6 | 96.1 | 102.9 | 107.5 |
| 13 | 1.91 | 31.36 | 108.1 | 97.6 | 104.3 | 114.5 |
| 14 | 0.99 | 130 | 94.5 | 91.5 | 101.9 | 105.6 |
| 15 | 2.18 | 52.47 | 93.7 | 90.2 | 101.9 | 107.8 |
| 16 | 1.92 | 62.33 | 98.3 | 94.3 | 103.1 | 107.6 |
| 17 | 2.33 | 89.02 | 98.1 | 94.6 | 102.4 | 105.1 |

The IR of the compounds was performed in a diamond cell in a transmittance mode in the FTIR Microscope:
Spectro-Tech Micro Sample Plan with Diamond Window, P.N. 0042-444;
NicPlan IR Microscope with MCT/A detector, 100 scans@4 cm$^{-1}$ Reflectachromat™ 15× objective.
FIG. 5 illustrates IR spectra of the dispersant of Example 3 which was prepared by reacting Unicid® 700 and polyethylenimine in a 1:1 ratio. FIG. 6 illustrates the IR spectra of the dispersant of Example 2 which was prepared by reacting Unicid® 700 and ethylenimine E-100 in a 2:1 ratio. FIG. 7 illustrates the IR spectra of the dispersant of Example 14 which was prepared by reacting Unicid® 700 and tetraethylenepentamine in a 1:1 ratio. FIG. 8 illustrates the IR spectra of the dispersant of Example 15 which was prepared by reacting Unicid® 700 and tetraethylenepentamine in a 2:1 ratio. Characteristic for the samples is the peak at 1648 cm$^{-1}$ C=O stretch (amide I) band of secondary amide, and the alkane $CH_2$ stretches at 2918 cm$^{-1}$ (asymmetric) and 2849 cm$^{-1}$ (symmetric).

Pigments Red 57:1, Pigment Yellow 155, Pigment Yellow 180, and Pigment Yellow 139, were used for the preparation of magenta and yellow ink Examples 18-31 which incorporated the aforementioned pigments and various pigment dispersant aids as disclosed herein. The ink base vehicle in all cases was formulated at nominal component levels and did not differ significantly ink to ink.

Comparative Example 18

The following components were used to make a jettable solid ink, the amounts of which are given as parts by weight unless otherwise stated. An ink concentrate base was prepared by mixing the following components by melting and homogeneously blending them together at 120° C. using an overhead stirrer: 37.53 parts of a distilled Polyethylene Wax from Baker Petrolite, 20.00 parts triamide wax (triamide described in U.S. Pat. No. 6,860,930, which is incorporated by reference herein in its entirety), 20.00 parts S-180® (a stearyl stearamide commercially available from Crompton Corporation), 20.00 parts KE-100® resin commercially available from Arakawa Corporation, triglycerides of hydrogenated abietic (rosin) acid, from Arakawa Chemical Industries, Ltd., 2.26 parts of Foral® 85, an ester of a hydrogenated resin, available from Hercules Incorporated, 0.21 parts Naugard® 445 available from Crompton Corporation, and 3.23 parts Solsperse® 17000, available from Lubrizol Corporation. A Szegvari 01 attritor pre-heated to 110° C. was charged with 1800 g ⅛" 440 C Grade 25 stainless steel balls, available from Hoover Precision Products, Incorporated, that were preheated to 120° C. The attritor was allowed to equilibrate for 30 minutes upon which 4.84 parts of pigment red 57:1 available from Clariant GmbH were added slowly to the ink base. A multi-staged impeller was then attached to the attritor and the speed adjusted to give an impeller tip velocity of about 7 cm/s. The pigmented mixture was allowed to attrite overnight for 19 hours upon which the resultant ink pigment concentrate showed excellent free-flowing behavior when it was discharged and separated from the steel balls in its molten state.

The ink of Comparative Example 18 was then made from the ink pigment concentrate discussed above. Specifically, a molten homogeneous solution of the following components mixture was prepared: 72.98 parts of a distilled Polyethylene Wax from Baker Petrolite, 3.70 parts triamide wax (triamide described in U.S. Pat. No. 6,860,930), 17.11 parts S-180® (a stearyl stearamide) commercially available from Crompton Corporation, 5.20 parts KE-100® resin commercially available from Arakawa Corporation, triglycerides of hydrogenated abietic (rosin) acid, from Arakawa Chemical Industries, Ltd., 0.23 parts Naugard® 445 available from Crompton Corporation, and 0.78 parts Solsperse® 17000, available from Lubrizol Corporation. This solution was added slowly to 74.9 g of the ink pigment concentrate in an oven at 120° C. while stirring at 400 RPM. The resulting pigmented ink was coarsely filtered at 120° C. past a 6 micron glass fiber filter available commercially from Pall Corporation. Thereupon the ink was filtered through a 1 micron glass fiber filter available commercially from Pall Corporation. The shear rate viscosity at 115° C. was measured on the 1 micron permeate of the ink using cone and plate method on an RFS3 rheometer available from Rheometrics Scientific. The ink was found to be Newtonian and had shear rate viscosities of 10.0 and 9.9 cP at 1 and 100 s$^{-1}$, respectively.

Magenta solid ink Examples 19-27 were formulated using dispersants of the present disclosure and pigment Red 57.1.

Example 19

An ink pigment concentrate was made in the same manner as in Comparative Example 18, except that in place of Solsperse® 17000, 3.23 parts of the dispersant of Example 3 were used.

From this ink pigment concentrate an ink was prepared. The making of this ink concentrate proceeded in the same manner as in Comparative Example 18, except that in place of Solsperse® 17000, 0.78 parts of dispersant Example 3 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The shear rate viscosity at 115° C. was measured on the 1 micron permeate of the ink using cone and plate method on an RFS3® rheometer available from Rheometrics Scientific. The ink was found to be Newtonian.

Example 20

An ink pigment concentrate was made in the same manner as in Comparative Example 18, except that in place of Solsperse® 17000, 3.23 parts of the dispersant of Example 6 were used.

From this ink pigment concentrate an ink was prepared. The making of this ink concentrate proceeded in the same manner as in Comparative Example 18, except that in place of Solsperse 17000®, 0.78 parts of dispersant Example 6 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The shear rate viscosity at 115° C. was measured on the 1 micron permeate of the ink using cone and plate method on an RFS3® rheometer available from Rheometrics Scientific. The ink was found to be Newtonian and had shear rate viscosities of 9.7 and 10.3 cP at 1 and 100 s$^{-1}$, respectively.

Example 21

An ink pigment concentrate was made in the same manner as in Comparative Example 18, except that in place of Solsperse® 17000, 3.23 parts of the dispersant of Example 4 were used.

From this ink pigment concentrate an ink was prepared. The making of this ink concentrate proceeded in the same manner as in Comparative Example 18, except that in place of Solsperse® 17000, 0.78 parts of dispersant Example 4 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The shear rate viscosity at 115° C. was measured on the 1 micron permeate of the ink using cone and plate method on an RFS3® rheometer available from Rheometrics Scientific. The ink was found to be Newtonian and had shear rate viscosities of 9.5 and 9.8 cP at 1 and 100 s$^{-1}$, respectively.

Ink Example 22

An ink pigment concentrate was made in the same manner as in Comparative Example 18, except that in place of Solsperse® 17000, 3.23 parts of the dispersant of Example 10 were used.

From this ink pigment concentrate an ink was prepared. The making of this ink concentrate proceeded in the same manner as in Comparative Example 18, except that in place of Solsperse® 17000, 0.78 parts of dispersant Example 10 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The particle size of the ink was measured using a Malvern Nanosizer® HT apparatus.

Ink Example 23

An ink pigment concentrate was made in the same manner as in Comparative Example 18, except that in place of Solsperse® 17000, 3.23 parts of the dispersant of Example 11 were used.

From this ink pigment concentrate an ink was prepared. The making of this ink concentrate proceeded in the same manner as in Comparative Example 18, except that in place of Solsperse® 17000, 0.78 parts of dispersant Example 11 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The particle size of the ink was measured using a Malvern Nanosizer® HT apparatus.

Ink Example 24

An ink pigment concentrate was made in the same manner as in Comparative Example 18, except that in place of Solsperse® 17000, 3.23 parts of the dispersant of Example 14 were used.

From this ink pigment concentrate an ink was prepared. The making of this ink concentrate proceeded in the same manner as in Comparative Example 18, except that in place of Solsperse 17000®, 0.78 parts of dispersant Example 14 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The particle size of the ink was measured using a Malvern Nanosizer® HT apparatus.

Ink Example 25

An ink pigment concentrate was made in the same manner as in Comparative Example 18, except that in place of Solsperse® 17000, 3.23 parts of the dispersant of Example 15 were used.

From this ink pigment concentrate an ink was prepared. The making of this ink concentrate proceeded in the same manner as in Comparative Example 18, except that in place of Solsperse® 17000, 0.78 parts of dispersant Example 15 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The particle size of the ink was measured using a Malvern Nanosizer® HT apparatus.

Ink Example 26

An ink pigment concentrate was made in the same manner as in Comparative Example 18, except that in place of Solsperse® 17000, 3.23 parts of the dispersant of Example 16 were used.

From this ink pigment concentrate an ink was prepared. The making of this ink concentrate proceeded in the same manner as in Comparative Example 18, except that in place of Solsperse® 17000, 0.78 parts of dispersant Example 16 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The particle size of the ink was measured using a Malvern Nanosizer® HT apparatus.

Ink Example 27

An ink pigment concentrate was made in the same manner as in Comparative Example 18, except that in place of Solsperse® 17000, 3.23 parts of the dispersant of Example 17 were used.

From this ink pigment concentrate an ink was prepared. The making of this ink concentrate proceeded in the same manner as in Comparative Example 18, except that in place of Solsperse® 17000, 0.78 parts of dispersant Example 17 were used. The resulting pigmented ink was coarsely filtered at 120° C. past a 6 μm glass fiber filter, available commercially from Pall Corporation. Thereupon the ink was filtered through a 1 micron glass fiber filter, available commercially from Pall Corporation. The particle size of the ink was measured using a Malvern Nanosizer® HT apparatus.

Yellow solid ink Examples were formulated using dispersants of the present disclosure and three different types of yellow pigments: ink Example 28 was formulated using pigment yellow 155, ink examples 29 and 30 were formulated using pigment yellow 180, ink example 31 was formulated using pigment yellow 139.

Ink Example 28

A yellow ink was prepared as follows. A Union Process 01 attritor pre-heated to 120° C. was charged with 1800 grams of ⅛" 440 C Grade 25 stainless steel balls, available from Hoover Precision Products, Incorporated, that were also pre-heated to 120° C. Over the steel shots was poured a molten mixture containing 41.36 parts triamide wax described in U.S. Pat. No. 6,860,930, which is hereby incorporated by reference herein in its entirety, 37.7 parts stearyl stearamide (Kemamide® 5-180, available from Chemtura Corporation), 9.3 dispersant example 1, and 11.6 parts pigment yellow 155 Available from Clariant). A multi-staged impeller was then attached to the attritor and the speed adjusted to about 300 RPM. The pigmented mixture was allowed to attrite overnight for 19 hours. The beaker containing the isolated pigment concentrate is maintained at 120° C., and the concentrate was then diluted over a period of 60 minutes with a molten resin mixture containing 77.2 parts distilled polyethylene wax available from Baker Petrolite, 1.9 parts Kemamide® S-180, 18.3 parts triglycerides of hydrogenated abietic acid (KE-100®, available from Arakawa Chemical Industries, Ltd.), 2.27 parts urethane resin described in U.S. Pat. No. 6,309,453, which is hereby incorporated by reference herein in its entirety, and 0.3 parts antioxidant (Naugard® N-445, available from Crompton Corporation). The resulting ink was allowed to stir for 90 minutes at 120° C. and was filtered past a 1 micron filter.

Ink Example 29

The yellow pigmented ink of Example 29 was prepared using the same process as described for ink example 28, except that 11.3 parts of pigment yellow 180 available from Clariant was used in place of pigment yellow 155. The resulting ink was allowed to stir for 90 minutes at 120° C. and was filtered past a 1 micron filter.

Ink Example 30

The yellow pigmented ink of Example 30 was prepared using the same process as described for ink example 28, except that 11.3 parts of pigment yellow 180 available from Clariant was used in place of pigment yellow 155 and 9.3 parts of dispersant example 14 was used in place of dispersant example 1. The resulting ink was allowed to stir for 90 minutes at 120° C. and was filtered past a 1 micron filter.

Ink Example 31

The yellow pigmented ink of Example 31 was prepared using the same process as described for ink example 28, except that 11.3 parts of pigment yellow 139 available from Clariant was used in place of pigment yellow 155 and 9.3 parts of dispersant example 14 was used in place of dispersant example 1. The resulting ink was allowed to stir for 90 minutes at 120° C. and was filtered past a 1 micron filter.

Table 3 shows the particle size measurements for the magenta comparative ink Example 18 and all magenta and yellow inks made with the dispersants of the present disclosure. Samples were aged in the oven at 120° C. and particle size was measured at 112° C. (jetting temperature) using the Malvern Zetasizer. As shown in Table 3, magenta ink Examples 19, 20, 21, 24, 26, and 27 made from dispersants of the present disclosure with an oligomeric anchoring unit (more than 3 NH) had stable particle size for at least 2 weeks, with ink 21 made from the dispersant of Example 4 showing particle size stability for over one year. The ink made from the commercial dispersant Solsperse® 1700 started showing particle size growth after 2 days. Inks 22 and 25 made from the dispersants of Examples 10 and 15, respectively, showed slight particle size growth after 18 and 39 days, respectively. Ink Example 23 from dispersant 11, which does not have any free NH groups, showed the most particle size growth, but it is still much more stable than ink Example 18 made from commercial dispersant Solsperse® 17 0000. These inks had few free NH groups (0-3) which are not bonded to the carbonyl group. Few HN groups results in a weaker anchoring unit as shown by particle size growth.

Yellow ink Examples 28-31 made from dispersant examples of this invention which have at least 3 free NH groups also showed stable particle size growth for at least 7 days.

TABLE 3

Particle Size of Neat Aged Magenta Solid Inks

| | | Thermal Stability at 120° C. | | |
|---|---|---|---|---|
| | | Z-average (nanometers) | | Number of |
| Ink | Pigment | Dispersant | Day zero | Last day | days aged |
| Magenta Inks | | | | | |
| 18 | PR57:1 | Solsperse ® 17000 | 141 | 300 | 3 |
| 19 | PR57:1 | Ex. 3(1:1 U700/PEI) | 138 | 132 | 70 |
| 20 | PR57:1 | Ex. 6(2:1 U550/PEI) | 172 | 172 | 14 |
| 21 | PR57:1 | Ex. 4(2:1 U700/PEI) | 158 | 158 | 363 |
| 22 | PR57:1 | Ex.10(1:1 U700/EDA) | 134 | 148 | 18 |
| 23 | PR57:1 | Ex. 11(2:1 U700/EDA) | 119 | 152 | 17 |
| 24 | PR57:1 | Ex.14(1:1U700/TEPA) | 132 | 134 | 39 |
| 25 | PR57:1 | Ex.15(2:1 U700/TEPA) | 121 | 148 | 39 |
| 26 | PR57:1 | Ex.16(1.5:1 U700/TEPA) | 118 | 128 | 45 |
| 27 | PR57:1 | Ex.17(1.5:1 U700/E-100) | 127 | 128 | 63 |
| Yellow Inks | | | | | |
| 28 | PY155 | Ex. 1(1:1U700/E-100) | 187 | 181 | 7 |
| 29 | PY180 | Ex. 1(1:1U700/E-100) | 261 | 226 | 9 |
| 30 | PY180 | Ex.14(1:1U700/TEPA) | 212 | 231 | 11 |
| 31 | PY139 | Ex. 14(1:1U700/TEPA) | 132 | 134 | 18 |

The magenta inks of Comparative Example 18 and Example 21 were also aged in the printer and prints were made and analyzed. The ink of Comparative Example 18 made using the commercial dispersant Solsperse® 1700 exhibited a phenomenon known as banding. Banding is non-uniform jetting that results in a decrease in optical density across the page. Optical density of prints made from this ink decreased significantly in five days. Prints made from the ink of Example 21 showed no banding and no significant change in optical density after aging in the printer for 10 days. The formulation and use of novel compounds as pigment dispersant aids into pigmented solid inks, such as containing PY155, PY180, PY139 and PR57:1, resulted in inks having excellent dispersibility, filterability, and thermal stability characteristics. The thermal stability assessment of many of the inks is still ongoing owing to the excellent thermal stabilities of same.

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims. Unless specifically recited in a claim, steps or components of claims should not be implied or imported from the specification or any other claims as to any particular order, number, position, size, shape, angle, color, or material.

The invention claimed is:

1. A compound of the formula

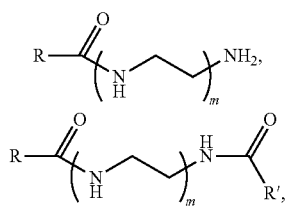

or a mixture thereof;

wherein R and R' are the same or different, and wherein R and R' are independently selected from a linear alkyl group having about 37 carbon atoms and a linear alkyl group having about 47 carbon atoms;

and wherein m is an integer of from about 1 to about 30.

2. The compound of claim 1, having the formula

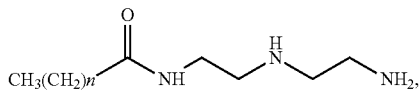

wherein n has an average value of about 46.

3. The compound of claim 1, having the formula

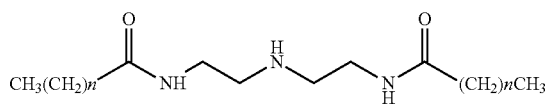

wherein n has an average value of about 46.

4. The compound of claim 1, having the formula

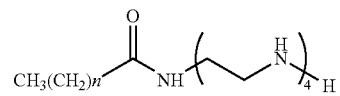

wherein n has an average value of about 46.

5. The compound of claim 1, having the formula

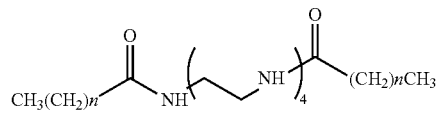

wherein n has an average value of about 46.

6. The compound of claim 1, having the formula

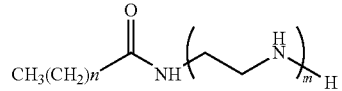

where n has an average value of about 46 and m is about 6.

7. The compound of claim 1, having the formula

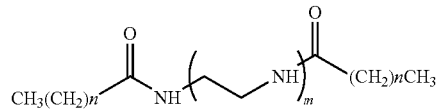

wherein n has an average value of about 46 and m is about 6.

8. The compound of claim 1, having the formula

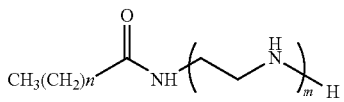

wherein n has an average value of about 46 and m is about 9.

9. The compound of claim 1, having the formula

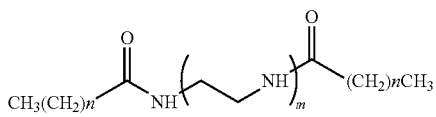

wherein n has an average value of about 46 and m is about 9.

10. The compound of claim 1, having the formula

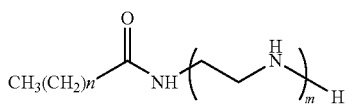

where n has an average value of about 46 and m is about 14.

11. The compound of claim 1, having the formula

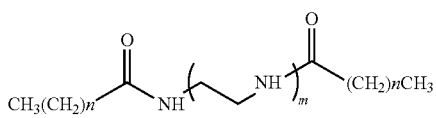

wherein n has an average value of about 46 and m is about 14.

12. The compound of claim 1, having the formula

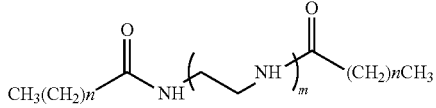

wherein n has an average value of about 36 and m is about 9.

13. A compound having the formula

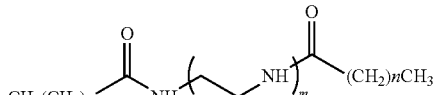

wherein n has an average value of about 28 and m is about 9.

14. A compound having the formula

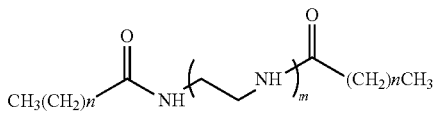

wherein n has an average value of about 20 and m is about 9.

15. The compound of claim 1, comprising a mixture of compounds of the formula

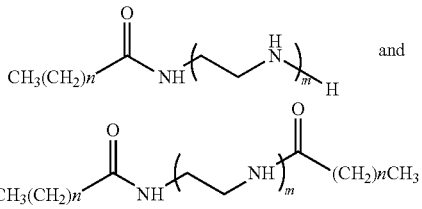

wherein n has an average value of 46 carbons and m is about 4.

16. The compound of claim 1, comprising a mixture of compounds of the formula

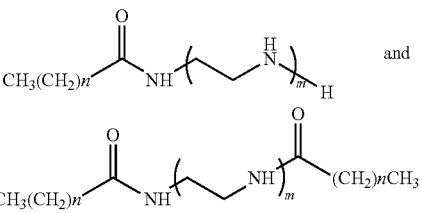

wherein n has an average value of 46 carbons and m is about 6.

17. A method for preparing a compound comprising:
melting a carboxylic acid of the formula

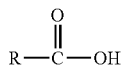

wherein R is (i) an alkyl group, which may be linear or branched, cyclic or acyclic, substituted or unsubstituted, and wherein hetero atoms either may or may not be present in the alkyl group,
(ii) an arylalkyl group, which may be substituted or unsubstituted, wherein the alkyl portion of the arylalkyl group can be linear or branched, cyclic or acyclic, substituted or unsubstituted, and wherein hetero atoms either may or may not be present in either the aryl or the alkyl portion of the arylalkyl group, or
(iii) an alkylaryl group, which may be substituted or unsubstituted, wherein the alkyl portion of the alkylaryl group can be linear or branched, cyclic or acyclic, substituted or unsubstituted, and wherein hetero atoms either may or may not be present in either the aryl or the alkyl portion of the alkylaryl group; under an inert atmosphere;
wherein the alkyl group, the arylalkyl group, or the alkylaryl group has from about 18 to about 60 carbon atoms; and reacting an amine compound of the formula

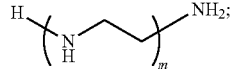

wherein m is an integer of from about 1 to about 30, with the melted carboxylic acid, under an inert atmosphere and at an elevated temperature of about 170 to about 200° C.;
  wherein the carboxylic acid and the amine are provided in a 2:1 ratio of carboxylic acid to amine, to provide a product of the formula

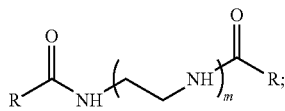   or wherein the carboxylic acid and the amine are provided in a 1:1 ratio of carboxylic acid to amine, to provide a product of the formula

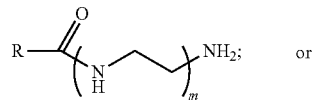   or wherein the carboxylic acid and the amine are provided in a 1.5:1 ratio of carboxylic acid to amine, to provide a product comprising a mixture of the formula

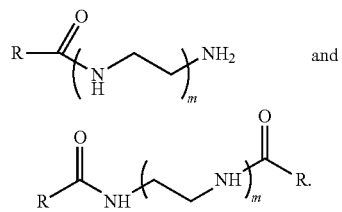

\* \* \* \* \*